United States Patent [19]

Scholz et al.

[11] Patent Number: 5,244,886

[45] Date of Patent: Sep. 14, 1993

[54] 11β-PHENYL-14βH STEROIDS

[75] Inventors: Stefan Scholz; Gunter Neef; Eckhard Ottow; Walter Elger; Sybille Beier; Krzysztof Chwalisz, all of Berlin, Fed. Rep. of Germany

[73] Assignee: Schering Aktiengesellschaft, Berlin und Bergkamen, Fed. Rep. of Germany

[21] Appl. No.: 663,819

[22] PCT Filed: Sep. 20, 1989

[86] PCT No.: PCT/EP89/01090

§ 371 Date: Mar. 20, 1991

§ 102(e) Date: Mar. 20, 1991

[87] PCT Pub. No.: WO90/03385

PCT Pub. Date: Apr. 5, 1990

[30] Foreign Application Priority Data

Sep. 20, 1988 [DE] Fed. Rep. of Germany ....... 3832303

[51] Int. Cl.$^5$ ............................ C07J 43/0; C07J 51/00; C07J 41/00; C07J 19/00

[52] U.S. Cl. .................................... 514/175; 514/176; 514/179; 514/180; 540/23; 540/41; 540/44; 540/47; 540/106; 540/107; 540/108; 540/114; 552/510; 552/511; 552/520; 552/540; 552/541; 552/544; 552/548; 552/553; 552/592; 552/593

[58] Field of Search ............... 514/175, 176, 179, 180; 552/511, 520, 540, 541, 544, 548, 510, 593, 592, 553; 540/41, 44, 47, 23, 108, 106, 107, 114

[56] References Cited

U.S. PATENT DOCUMENTS 4,386,085  5/1983  Teutsch et al. ...................... 514/176
4,954,490  9/1990  Cook et al. .......................... 514/176

FOREIGN PATENT DOCUMENTS 57115    8/1982   European Pat. Off. ............ 514/176
116974   8/1984   European Pat. Off. ............ 514/176
129499  10/1984   European Pat. Off. ............ 514/176
277676   8/1988   European Pat. Off. ............ 514/180
283428   9/1989   European Pat. Off. ............ 552/510
881962  10/1988   South Africa ...................... 552/510
9014354 11/1990   World Int. Prop. O. ........... 552/510

OTHER PUBLICATIONS

Grant and Hackh's Chemical Dictionary (New York, McGraw-Hill Books, 1987) p. 14.

Primary Examiner—Mukund J. Shah
Assistant Examiner—E. C. Ward
Attorney, Agent, or Firm—Millen, White, Zelano & Branigan

[57] ABSTRACT

New 11β-phenyl-14βH-steroids of general formula (I), where Z is an oxygen atom or the hydroxyimino-grouping N~OH, and M and N are either jointly a second compound or L is a hydrogen atom and M is an α-permanent hydroxy group and either A and B together are a second compound and D is a hydrogen atom, where $R^1$ is a five or six-part heteroalkyl residue or a cycloalkyl, cycloalkenyl or aryl residue or A is a hydrogen atom and B and D together are a methylene bridge, where $R^1$ besides the aforementioned residues may be a possibly substituted hydrocarbon residue with up to 10 C atoms, a possibly substituted amino group, a hydroxy or $C_{1-8}$ alkoxy, mercapto or thioalkyl group, $R^2$ is a methyl or ethyl residue, and $R^3/R^4$ represents the usual combination of substituents on the C17 atom in steroid chemistry, having antigestagenic and other properties.

16 Claims, No Drawings

11β-PHENYL-14βH STEROIDS

DESCRIPTION

This invention relates to 11beta-phenyl-14betaH steroids of general formula I

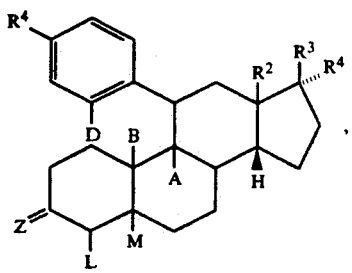

in which

Z stands for an oxygen atom or the hydroxyimino grouping N OH as well as L and M either together stand for a second bond or L for a hydrogen atom and M for an alpha-position hydroxy group and either A and B together mean a second bond and D means a hydrogen atom, and $R^1$ stands either a) for a heteroaryl radical of formula Ia

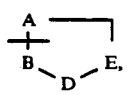

and A=N, O or S and B-D-E mean the element sequence C—C—C—, N—C—C or C—N—C, or b) stands for a heteroaryl radical of formula Ib

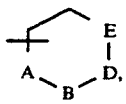

and A=N and B-D-E mean the element sequence C—C—C—, N—C—C, C—N—C or C—C—N or c) stands for cycloalkyl, cycloalkenyl or aryl radical Ic or else A means a hydrogen atom and B and D together mean a methylene group bridging the C 10 atom of the steroid skeleton and the ortho-carbon atom of the 11beta phenyl ring, and then Z additionally stands for 2 hydrogen atoms and $R^1$ has the meaning indicated above in this claim under a), b) or c) or d) stands for a straight-chain, branched, saturated or unsaturated hydrocarbon radical with up to 10 carbon atoms or e) stands for

with R' and R" meaning hydrogen or alkyl with 1 to 4 carbon atoms or R' and R" with the inclusion of N meaning a saturated 5- or 6-membered ring, and in the ring can contain another heteroatom such as O, N, S besides N, as well as the corresponding tertiary N oxides and the acid addition salts or f) stands for OR''' with R'''=H, $C_1$-$C_8$ alkyl or g) stands for $SR^{IV}$ with $R^{IV}$ meaning R''' or h) stands for a straight-chain, branched, saturated or unsaturated hydrocarbon radical with up to 10 carbon atoms, which is substituted with one or more oxo, hydroxyimino, $C_1$-$C_{10}$ acyloxy or $OR^V$ group(s) with $R^V$ meaning a hydrogen atom or a $C_1$-$C_8$ alkyl radical, and optionally the heteroaryl radical of formula Ia is substituted by one or more halogen radicals and/or one or more alkyl radicals with 1 to 3 carbon atoms and cycloalkyl, cycloalkenyl or aryl radical Id is substituted by one or more halogen, optionally protected hydroxy, alkoxy, optionally in the form of the sulfoxide or sulfone and/or of the N oxide, oxidized alkylthio and/or dialkylamino radicals, $R^2$ stands for a methyl or ethyl radical, $R^3$/$R^4$ stand for

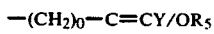

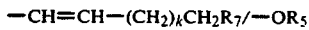

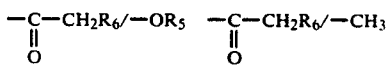

as well as

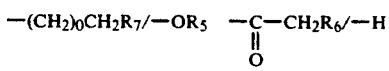

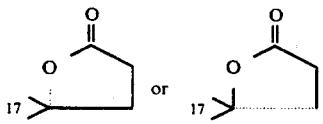

with $R_5$ meaning a hydrogen atom or acyl radical with 1 to 4 carbon atoms and Y means a hydrogen, chlorine, iodine or bromine atom, an alkyl, hydroxyalkyl, alkoxyalkyl or acyloxyalkyl group with 1 to 4 carbon atoms each in the alkyl or acyl radical $R_6$ stands for a hydrogen atom, a hydroxy group, an alkyl, O alkyl or O acyl group with 1 to 4 carbon atoms each, O stands for the numbers 0, 1, 2 or 3, $R_7$ stands for a hydroxy or cyanide radical, an O alkyl or an O acyl group with 1 to 4 carbon atoms each, k stands for the numbers 0, 1 or 2 and Q stands for an oxygen atom or two hydrogen atoms.

As a special feature the compounds of this invention, deviating from naturally occurring steroids, exhibit a beta-position hydrogen atom on the 14 carbon atom. Such 14beta H steroids have already recently become known to a limited extent from European patent application 0 277 676. These known compounds with $\Delta^{4,9}$-3-keto steroid skeleton exhibit in the 11 position a p-substituted (hetero)aryl ring. There are described as p-substituents: optionally saturated or unsaturated, straight-chain or branched hydrocarbon radicals with 1-10 carbon atoms, and the hydrocarbon radical additionally can also carry a hydroximino, oxo and/or hydroxy group of an amino group —NXY, with X and Y=H or $C_1$-$C_4$ alkyl, and if X and Y=alkyl, these, together with N, can also form a heterocyclic 3- to 7-ring.

The substitution pattern obtainable according to EP-A 0 277 676 on the 11beta phenyl ring is relatively limited. The search for other 14beta H steroids, which exhibit substituents on the 11beta phenyl ring exceeding EP-A 0 277 676, therefore seems urgently necessary to achieve compounds which, for example, with regard to their antigestagen action, are superior to those of EP-A 0 277 676.

The new compounds of general formula I as well as their pharmaceutically compatible addition salts with acids are valuable pharmaceutical agents. Thus, they have a strong affinity for the gestagen receptor and have antigestagen properties.

The antiglucocorticoid effectiveness is just slightly pronounced or no longer present at all (in comparison with the 11beta-(4-dimethylaminophenyl)-17beta-hydroxy-17alpha-(propin-1-yl)-4,9(10)-estradien-3-one (RU 486) known from EP-A 0 057 115).

The affinity of the compounds according to the invention for the counterreceptor is examined in the gestagen receptor binding test. Here the displacement of the agonist by the antagonist is measured.

Cytosol from rabbit uterus homogenate, which contains the receptor molecule—a protein—is used. The latter binds progesterone with great affinity and little capacity. If these receptors are loaded with $^3$H progesterone in the presence of the unlabeled substance to be tested, it depends on the concentration and the binding affinity of the compound to be examined, how strongly the $^3$H progesterone is displaced from the receptor. After separation of the receptor-bound progesterone from the unbound, the binding can be determined in percent and this value is plotted against the logarithm of the molar concentration of the test substance. Characteristic dose-dependent displacement curves are obtained and now the concentration of the test substance that is necessary to displace the reference substance completely from the receptor can be determined. The competition factor K as a measurement for the binding strength is defined as the ratio of the concentration of the test substance to the concentration of the reference substance (progesterone), at which both compounds show an equally great displacement of the $^3$H progesterone from the progesterone-receptor complex.

TABLE 1

| Gestagen Receptor Binding Test | |
|---|---|
| Compound | Rabbit Uterus K (gestagen) |
| A | 11.2 |
| B | 4.2 |
| C | 15 |
| D | 7 |
| E | 13 |
| F | 5.5 |

A = 11beta-(4-acetylphenyl)-17alpha-hydroxy-17-(prop-1-inyl)-14beta-estra-4,9-dien-3-one.
B = 11beta-(4-acetylphenyl)-17alpha-hydroxy-17-(prop-2-inyl)-14beta-estra-4,9-dien-3-one.
C = 17-hydroxy-17beta-(3-hydroxypropyl)-11beta,19-(4-methoxy-o-phenylene)-14beta-androst-4-en-3-one.
D = 17-hydroxy-17beta-(3-hydroxypropyl)-11beta,19-(4-(3-pyridyl)-o-phenylene]-14beta-androst-4-en-3-one.
E = 17-hydroxy-17beta-(3-hydroxypropyl)-11beta,19-(4-vinyl-o-phenylene)-14beta-androst-4-en-3-one.
F = 11beta-(4-dimethylaminophenyl)-17alpha-hydroxy-17-(3-hydroxypropyl)-14beta-estra-4,9-dien-3-one. (comparison compound. EP-A 0 277 676).

Such active ingredients with antigestagen activity can be used first of all for the treatment of hormone-dependent tumors that exhibit progesterone receptors in their tissue. Preferred indication in this connection is the treatment of breast cancer.

But they are also suitable for inducing abortions, since they displace from the receptor the progesterone necessary for maintaining the pregnancy. They can also be used for postcoital fertility control, inducing menstruation and labor. Finally, they can also be used for treatment of hormonal irregularities.

The antiproliterative potency of progesterone antagonists on the mammary gland was determined in a bioassay. For this purpose, ovariectomized rats were substituted for 3 days with estrone (10 micrograms) and progesterone (3 mg) and another group at the same time was treated with the following progesterone antagonists (1 mg/animal/day):

G: 11beta-(4-acetylphenyl)-17beta-hydroxy-17alpha-(1-propinyl)-4,9-estradien-3-one,
H: 11beta-[4-(3-pyridyl)phenyl]-17alpha-hydroxy-17-(3-hydroxypropyl)-14beta-estra-4,9-dien-3-one,
I: 11beta-(4-dimethylaminophenyl)-4,5-dihydro-spiro[1-4beta-estra-4,9-diene-17alpha,2'(3'H)-furan]-3-one (EP-A-0 277 676).

The entire inguinal mammary gland was dissected by performance of the "whole mount" technique (Lyons and Johnson, 1952). Of six animals, the number of tubulo-alveolar gland end pieces is determined by 40 times magnification.

The antiproliferative potency is expressed in percent of the inhibition of the tubulo-alveolar end pieces corresponding to the following formula:

(estrone $(E)$+progesterone $(P))-(E+P+G)=100\%$
of treated animals $(E+P)-$(test compound $H$ or $I)=X\%$ $100\%-X\%=\%$ inhibition G: 100 inhibition
H: 92% inhibition
I: 13% inhibition

TABLE 2

Antiglucocorticoid effectiveness of compounds A to G; the effectiveness is indicated in % of th effectiveness of RU 486 (effectiveness 100%)

| Compound | Antiglucocorticoid effectiveness (in % of RU 486) |
|---|---|
| A | 1 |
| B | 1 |
| C | 0 |
| D | 0 |
| E | 1 |
| F | 2 |

Thus the invention also relates to pharmaceutical agents on the basis of pharmaceutically compatible—i.e., nontoxic in the doses used—compounds of general formula I as well as their addition salts with pharmaceutically compatible acids, optionally together with the usual auxiliary agents and vehicles.

The compounds according to the invention and their salts can be processed according to methods of galenical medicine known in the art into pharmaceutical preparations for enteral, percutaneous, parenteral or local application. They can be administered in the form of tablets, dragees, gel capsules, granules, suppositories, implants, injectable sterile aqueous or oily solutions, suspensions or emulsions, ointments, creams and gels.

In this case the active ingredient or ingredients can be mixed with auxiliary agents usual in galenicals such as, e.g., gum arabic, talc, starch, mannitol, methylcellulose, lactose, surfactants such as Tweens ® or Myrj ®, magnesium stearate, aqueous or nonaqueous vehicles, paraffin derivatives, wetting, dispersing, emulsifying agents, preservatives and flavors for taste correction (e.g., essential oils).

Thus, the invention also relates to pharmaceutical compositions, which contain at least one compound according to the invention or one of its pharmaceutically compatible addition salts with acids as active ingredient.

Hydrochlorides and methane sulfonates can especially be mentioned as addition salts of products with acids according to the invention.

A dosage unit contains about 1–100 mg of active ingredient(s).

The dosage of the compounds according to the invention in humans is about 1–1000 mg per day.

The 3-thienyl, 3-furyl and 3-pyrrol radicals are preferred of the possible heteroaryl radicals according to formula Ia.

The 3- or 4-pyridyl, the 5-pyrimidine, 4-pyridazine or pyrazine radical are especially suitable according to the invention as heteroaryl radicals of formula Ib.

The cyclohexyl, the cyclohex-1-enyl, cyclohex-2-enyl, cyclohex-3-enyl as well as the phenyl radical can be especially emphasized as cycloalkyl, cycloalkenyl or aryl radical Ic.

The hydrocarbon radical according to formula I mentioned under d) or h) is to exhibit in the unsaturated case preferably up to 3 double bonds.

Especially a chlorine or bromine atom can be mentioned as halogen substituents, which are possible on the heteroaryl radical of formula Ia.

If the heteroaryl radical of formula Ia is alkyl substituted, the monosubstitution is preferred.

The cyloalkyl, cycloalkenyl or aryl radical Ic can be substituted by one or two chlorine and/or bromine atom(s). Said radicals can also be substituted by one or two, optionally protected hydroxy and/or alkoxy radicals with 1 to 8 carbon atoms.

The alkyl groups with 1–4 carbon atoms occurring in

are preferably methyl, ethyl and/or propyl. If R' and R" together form, with the inclusion of the nitrogen atom, a heterocyclic five or six ring, which, besides N and C atoms, can additionally also contain an O or S atom, there can be mentioned here the pyrrole, pyrrolidine, piperidine, piperazine, morpholine, oxa and thiazolidine as well as thiadiazolidine ring.

The methyl group is preferred as $R^2$ substituent according to the invention.

Of the combinations according to the invention possible for $R^3/R^4$, none is to be especially emphasized, but the methyl, ethyl, propyl or formyl, acetyl, propionyl as well as butyryl groups are preferred for the alkyl and/or acyl groups occurring in $R^5$, Y, $R^6$ and $R^7$.

Two possible cases according to the invention can be distinguished relative to substituents A, B and D.

1) A and B together form a second bond between carbon atoms 9 and 10, and D stands for a hydrogen atom. The $\Delta^{4,9}$-3-keto-11beta-phenyl-14beta-H-steroids of general formula I' are reached

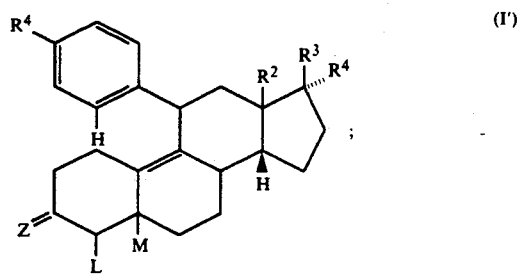

$R^1$ here stands, as already indicated, for a five- or six-membered heteroaryl radical of formula Ia or Ib or for a cycloalkyl, cycloalkenyl or aryl radical Ic.

2) A stands for a hydrogen atom and B and D form together a methylene group bridging the C-10 atom and the O carbon atom of the 11beta phenyl ring. The $\Delta^4$-3-keto-19,11beta-o-phenylene-14beta-H-steroids of general formula I" are reached

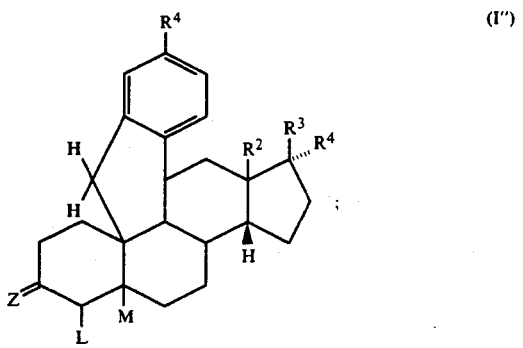

Additionally to the substituents already indicated under formula I' for $R^1$, $R^1$ also stands for the substituents described in formula I under d) to h).

Finally, both in formula I' and in I", L and M stand for a second bond between the C-3 and C-4 atom or L stands for an H atom and M for an alpha-position hydroxy group.

The new compounds of general formula I are produced according to the invention, by a compound of general formula II

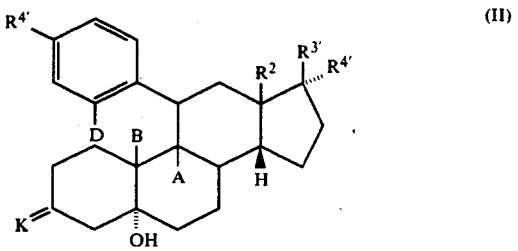

in which

A, B, D and $R^2$ have the meaning indicated in formula I,

K means a blocked keto group in the form of the ketal or thioketal, $R^{1'}$ either has the meaning indicated in $R^1$ under a) to g), or a straight-chain or branched, saturated or unsaturated alkyl radical with 1 to 10 carbon atoms, which contains the grouping

in the protected form

with K having the meaning indicated above or K means a hydrogen atom and an optionally protected hydroxy group, as well as $R^{3'}$ and $R^{4'}$ have the same meaning as $R^3$ and $R^4$ in formula I, and present hydroxy and/or acyl and/or terminal alkyne groups are optionally protected, being subjected to the action of a dehydration agent, which is also capable of releasing the 3-oxo group and the protected keto groups present in $R'$, optionally with formation of the 4(5) double bond, the resulting product optionally being freed from other protecting groups and optionally being reacted with hydroxylamine hydrochloride to the product of general formula I with Z meaning the hydroxyimino grouping N~OH.

The release of the 3-keto function with simultaneous water cleavage and formation of the 4(5) double bond takes place by treatment with acid or an acid ion exchanger. The acid treatment takes place in a way known in the art by the corresponding 5alpha-hydroxy-3-ketal being dissolved in a water-miscible solvent, such as aqueous methanol, ethanol or acetone, and by catalytic amounts of mineral or sulfonic acid, such as hydrochloric acid, sulfuric acid, phosphoric acid, perchloric acid or p-toluenesulfonic acid, or an organic acid such as acetic acid, acting on the solution until the present protecting groups are removed and optionally water is cleaved. The reaction, which takes place at temperatures from 0° to 100° C., can also be performed with an acid ion exchanger. The course of the reaction can be followed with analytic methods, for example by samples removed by thin-layer chromatography.

In general, protecting group removal and water cleavage are performed in one reaction step, by the corresponding 5alpha-hydroxy-3-ketal or 5-en-ketal being reacted in a strongly acid medium for a certain time. But it is possible equally well according to the invention for the protecting group removal and water cleavage to be performed in two reaction steps separate from one another, by the corresponding 5alpha-hydroxy-3-keto compound first being recovered by a shorter treatment of the corresponding 5alpha-hydroxy-3-ketal in moderately acid medium and optionally being isolated. The 5alpha-hydroxy-3-keto compound is then converted into the 3-keto-4-ene compound by allowing acid to continue to act with water cleavage.

Various synthesis methods are possible for the production of the initial products of general formula II. To achieve the compounds both of general formulas II' and II'' (by compounds of formulas II' and II'' are to be understood those that finally lead to the end compounds of formula I' or the bridged compounds of formula I''), according to the invention the synthesis indicated in the reaction scheme I below is suitable.

Production of the initial compounds of formula II is especially achieved with the indicated, widely used process, in which $R^{1'}$ and/or $R^{3'}$ and/or $R^{4'}$ can be substituents exhibiting one more C—C multiple bonds, since they are introduced only after hydrogenation of VII→VIII.

Production of starting compound III is described in EP-A-O 127 864; $R^2$ and K have the meaning indicated in formula II.

By Grignard addition (Tetrahedron Letters 1979, 2051) of aryl halides

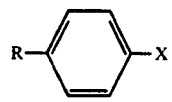

and 2-halogen aryl methyl halides

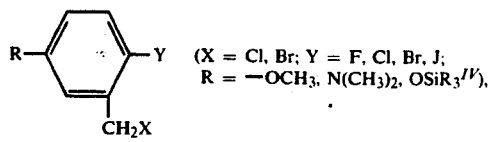

in which the addition products in the last mentioned case are still subjected to a reductive cyclization reaction (Birch reduction with Li/NH₃ or reduction with Bu₃SnH), the compounds of general formula IV are achieved (example 1; production of the initial compound).

Reaction scheme I
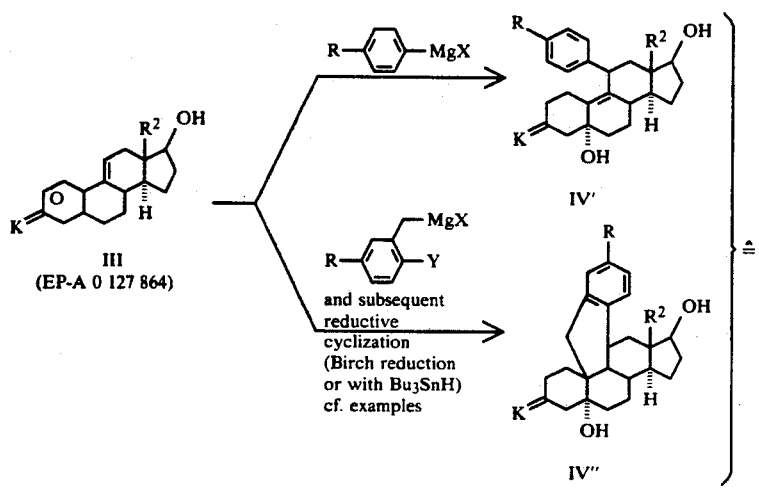
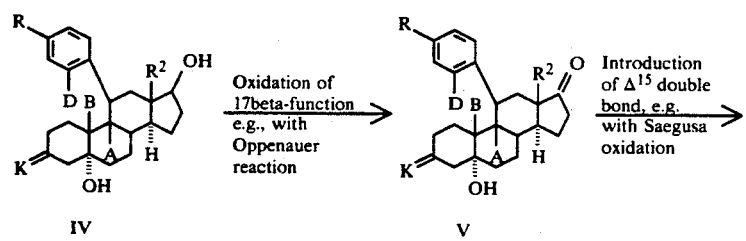
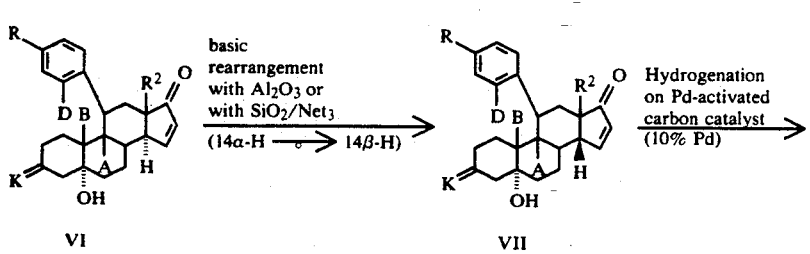
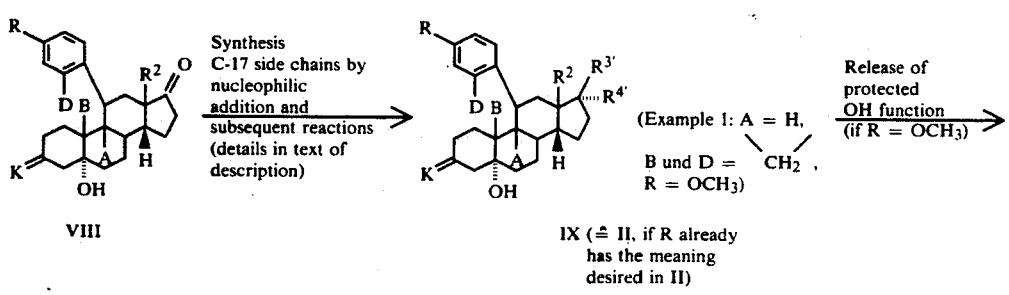

-continued
Reaction scheme 1

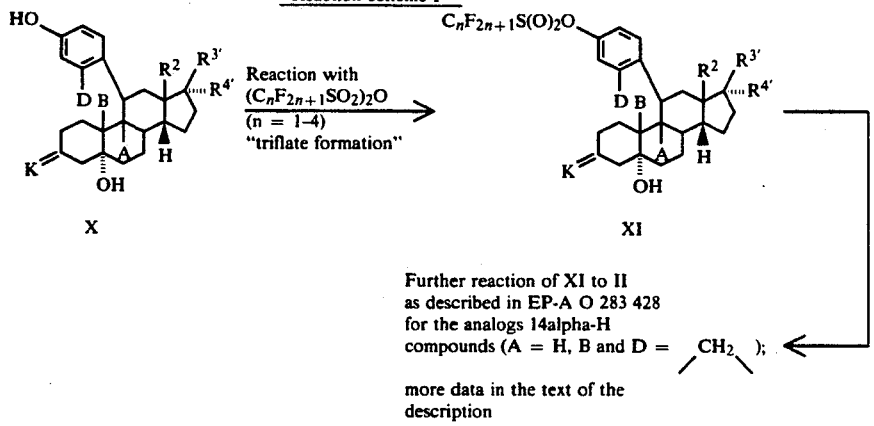

Further reaction of XI to II
as described in EP-A 0 283 428
for the analogs 14alpha-H
compounds (A = H, B and D = CH$_2$);
more data in the text of the description Oxidation of the C-17 hydroxy to the 17-keto group (e.g., Oppenauer oxidation) leads to compounds of general formula V.

The intermediate compounds of formula VI with an unsaturated D ring are accessible, for example, by modified Saegusa oxidation [Tetrahedron 42 (1986) 2971] of the corresponding enol compounds of the 17-ketone. For example, the trimethylsilylenol ether can be produced by conversion of the 17-ketone with lithium diisopropylamide in tetrahydrofuran to the corresponding enolate and trapping by trimethylchlorosilane (Synthesis 1983, 1).

By basic treatment of VI, for example by stirring with basic aluminum oxide or with silica gel/triethylamine in an inert solvent, the latter rearranges into the corresponding steroid with beta-position 14H of formula VII. The $\Delta^{15}$ double bond is subsequently again removed by hydrogenation on palladium/activated carbon catalyst (10% Pd).

The introduction of the substituents R$^{3'}$ and R$^{4'}$ takes place, after the usual process of the C-17 side chain synthesis, by nucleophilic addition on the 17-ketone III and subsequent reactions ("Terpenoids and Steroids," Specialist Periodical Report, The Chemical Society, London, Vol. 1–12).

Introduction of the substituent —C≡C—Y as R$^{3'}$, in which Y has the meaning indicated above, takes place with the help of a compound of general formula MC≡C—Y', in which Y' is the radical Y protected with a protecting group, such as, for example, trimethyl silyl or tert-butyl dimethyl silyl, or else if Y is an alkyl group with 1–4 C atoms, Y' itself is the radical Y.

The organometallic compound can also be formed in situ and be reacted with the 17-ketone. Thus, for example, acetylene and an alkali metal, especially potassium, sodium or lithium, in the presence of an alcohol or in the presence of ammonia, can be allowed to act on the 17-ketone in a suitable solvent. The alkali metal can also act in the form, for example, of methyl or butyl lithium. Dialkyl ether, tetrahydrofuran, dioxane, benzene and toluene are especially suitable as solvents.

The introduction of 3-hydroxy-propine, -propene or -propane into the 17 position takes place by reaction of the 17-ketone with the dianion of propargyl alcohol (3-hydroxypropine), for example, the dipotassium salt of the propargyl alcohol generated in situ, to 17alpha-(3-hydroxyprop-1-inyl)-17beta-hydroxy derivative or with metallized derivatives of 3-hydroxypropine, for example with 1-lithium-3-(tetrahydropyran-2'-yloxy)-prop-1-in-1-ide, to 17-[3-(tetrahydropyran-2'-yloxy)-prop-1-inyl]-17beta-hydroxy derivative, which can then be hydrogenated to the 17-(3-hydroxypropyl or hydroxypropenyl)-17beta-hydroxy compounds. This is achieved, for example, by hydrogenation at room temperature and normal pressure in solvents such as methanol, ethanol, propanol, tetrahydrofuran (THF) or ethyl acetate with addition of noble metal catalysts such as platinum or palladium.

Introduction of homologous hydroxyalkyne, hydroxyalkene and hydroxyalkane groups takes place in a corresponding way with homologs of the propargyl alcohol.

The compound with the Z-configured double bond in the hydroxypropenyl group is produced by hydrogenation of the acetylenic triple bond with a deactivated noble metal catalyst (J. Fried, J. A. Edwards: Organic Reactions in Steroid Chemistry, Van Nostrand Reinhold Company 1972, p. 134; and H. O. House: Modern Synthetic Reactions, 1972, p. 19). Suitable as deactivated noble metal catalysts are, for example, 10% palladium on barium sulfate in the presence of an amine or 5% palladium on calcium carbonate with addition of lead(II) acetate. Hydrogenation is discontinued after absorption of an equivalent of hydrogen.

The compound with the E-configured double bond in the hydroxypropenyl group is produced by reduction of the acetylenic triple bond in a way known in the art. A whole series of methods for conversion of alkines to trans-olefins are described in the literature, for example, the reduction with sodium in liquid ammonia (J. Am. Chem. Soc. 63 (1941) 216) with sodium amide in liquid ammonia (J. Chem. Soc. 1955, 3558), with lithium in low molecular amines (J. A. Chem. Soc. 77 (1955) 3378), with boranes (J. Am. Chem. Soc. 93 (1971) 3395 and 94 (1972) 6560), with diiosbutylaluminum hydride and methyl lithium (J. Am. Chem. Soc. 89 (1967) 5085) and especially with lithiumaluminum hydride/alcoholate (J. Am. Chem. Soc. 89 (1967) 4245). A further possibility is the reduction of the triple bond with chromium(II) sulfate in the presence of water or dimethylformamide in slightly acidic medium (J. Am. Chem. Soc. 86 (1964) 4358) as well as generally the reduction by action of transition metal compounds with change of the oxidation stage.

Introduction of the hydroxyalkenes can also take place directly by addition of a corresponding metallized hydroxyalkenyl compound, such as, for example, 1-lithium-3-(tetrahydropyran-2'-yloxy)-prop-1(E)-ene (J.

Org. Chem. 40 2265) or 1-lithium-3-(tetrahydropyran-2'-yloxy)-prop-1(Z)-ene (Synthesis 1981, 999). Homologs can also be introduced in this way.

Introduction of 3-hydroxy-propane as well as -butane in the 17 position can also take place directly by reaction of the 17-ketone with metallized derivatives of 3-halo-propanols or—butanols—in which the hydroxy group in the metallization step is present as alcoholate (Tetrahedron Letters 1978, 3013) or as protected function (J. Org. Chem. 37, 1947)—to the 17-(3-hydroxypropyl)-17beta-hydroxy compound or to compound protected on the terminal hydroxy group. Ethoxyethyl, tetrahydropyranyl and methoxymethyl groups, for example, are suitable as protecting groups.

Synthesis of the 17-cyanomethyl side chain takes place in a way known in the art from the 17-ketone, for example, by the 17-spiroepoxide and cleavage of the spiroepoxide with HCN according to Z. Chem. 18 (1978) 259–260.

Also the introduction of the 17-hydroxyacetyl side chain takes place according to methods known in the art, for example according to the methods described in J. Org. Chem. 47 (1982), 2993–2995, Chem. Ber. 113 (1984), 1184 or U.S. Pat. No. 4,600,538.

If end products of formula I are desired with $R^3/R^4$ meaning

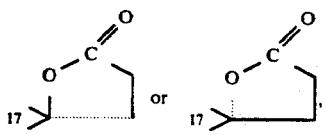

the 17-(3-hydroxypropyl) compound is oxidized in a way known in the art, for example, with Jones reagent, manganese dioxide, pyridinium dichromate, pyridinium chlorochromate, chromic acid pyridine or Fetizon reagent silver carbonate/Celite (Compt. rend. 267 [1968] 900).

Cyclization of the 17-(3-hydroxypropyl) or 17-(3-hydroxypropenyl) compounds according to known processes yields the corresponding saturated or unsaturated cyclic ether.

For the introduction of the groupings

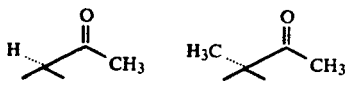

the 17-ketone is converted with tosylmethyl isocyanide (Chem. Ind. 1972 213) to the 17-nitrile compound (Tetrahedron 31 (1975) 2151), which can be converted directly with methyllithium or methylmagnesium bromide to the 17-acetyl compound, which yields the desired 17alpha-methyl-17beta-acyl grouping after enolization with K-tert-butylate in tetrahydrofuran and reaction with methyl iodide. This sequence of methyl addition on the nitrile and then alkylation can also be performed in reverse order.

Present free hydroxy or hydroxy, mercapto and/or amino groups can be alkylated or acylated in a way known in the art.

Sulfides and/or dialkylamines can be converted by suitable oxidation agents (for example, hydrogen peroxide or peracids) to the desired sulfoxides (n=1), N oxides (n=1) [see, e.g., Kontakte (Darmstadt) 1986,3, p. 12] or sulfones (n=2).

Compounds with a dialkylamine substituent in $R^{1'}$ can be converted in good yield to the corresponding (N-cyano-N-alkylaminoaryl) derivatives by reaction with bromocyanogen in aprotic solvents such as, for example, dioxane, benzene or toluene at elevated temperatures (amine decomposition according to Braun) analogously to the instructions indicated, for example, in Org. Reactions 7, 198 (1953), K. W. Bentley, Techniques of Organic Chemistry 11, 773 (1963) and Houben-Weyl, 5/4 151 (1960).

The latter, depending on the ultimately desired meaning of $R^1$ in the end product, are reduced in a way known in the art to the corresponding dialkylamino compounds (for example, with diisobutylaluminum hydride in toluene to the N-formyl-N-alkylaminophenyl intermediate products and then with lithiumaluminum hydride) or N—H—N-alkyl compounds (for example, with lithiumaluminum hydride or with lithium in liquid ammonia). The latter are then optionally acylated in a way known in the literature and then optionally reduced to the new dialkylamino derivative in a way known in the art, for example, with lithiumaluminum hydride (see DE 36 23 038).

As an example for a representative of the compounds of general formula IX, the preparation of 3,3-(2,2-dimethyltrimethylenedioxy)-11beta,19-(4-methoxy-o-phenylene)-17-[3-(tetrahydropyran-2-yloxy)-propyl]-14beta-androstane-5alpha,17alpha-diol is described in example 1d).

By release of the protected hydroxy group and reaction with perfluoroalkylsulfonic acid anhydride [alkyl with 1 to 4 carbon atoms; P. J. Stang, M. Hanack and L. R. Subramanian, Synthesis 85 (1982)] the "key compounds" of general formula XI (cf. also Example 1) are reached by compounds of general formula X.

In the compounds of general formula XI, as described in EP-A 0 283 428 for the analogous (bridged) 14alpha-H steroids, the trifluoroalkylsulfonic acid initial group can be exchanged, to reach compounds of general formula II, in which $R^{1'}$ has a meaning according to the invention other than R.

In the conversion of the trifluoroalkylsulfonate compounds of formula XI to compounds of formula II either the procedure is such that in a transition metal catalyzed reaction (preferably Pd⁰) the perfluoroalkylsulfonate starting group is displaced with essentially almost simultaneous substitution by the desired substituent $R^{1'}$ or its precursor, for example by allowing the reaction with tributylvinyl, tributylallyl or tributyl-1-ethoxyvinyltin or with another trialkyltin derivative containing the desired substituent (J. E. McMurry and S. Mohanraj, Tetrahedron Letters, 24, No. 27, pp. 2723–2726, 1983; X. Lu and J. Zhu, Communications, pp. 726–727, 1987; Q. Y. Chen and Z. Y. Yang, Tetrahedron Letters 27, No. 10, pp. 1171–1174, 1986; S. Cacchi, P. G. Ciattini; E. Morera and G. Ortar, Tetrahedron Letters, 27, No. 33, pp. 3931–3934, 1986; A. M. Echavarren and J. K. Stille, J. Am. Chem. Soc. 1987, 109, pp. 5478–5486), or intermediately a corresponding triorganylstannyl, preferably, tri-n-alkylstannyl compound, is produced from the perfluoroalkylsulfonate compound [J. K. Stille, Angew. Chem. 98 (1986), pp. 504–519). The latter is then transition metal catalyzed in a one-pot reaction with a halogen, preferably bromine or iodine substituted carbocyclic or heterocyclic aromatic substance [Y. Yamamoto, Y. Azuma, H. Mitoh, Communications, pp. 564–565, 1986; T. J. Bailey, Tetrahedron Letters, 27, No. 37, pp. 4407–4410, 1986], which optionally can carry still other substituents, reacted to a compound of general formula II; the phenyl radical exhibits in it the desired substitution or a precursor of the desired substitution. The tri-n-alkylstannyl compounds (alkyl=butyl) occurring intermediately, producible, for example, with hexabutylditin, can optionally be isolated.

The compounds of formula II', but in which $R^{1'}$ then cannot stand for a cycloalkenyl radical, are also reached by the reaction sequence indicated below in reaction scheme II. Since a cycloalkenyl radical could not survive undamaged the hydrogenation of XVI-XVII, the corresponding 11beta-(4-cycloalkenyl)-phenyl steroids cannot be produced in this way.

To illustrate the variant indicated in reaction scheme II, example 2 reproduces in a representative way the production of 17alpha-hydroxy-17-(I-propinyl)-11beta-[4-(2-thiazolyl)-phenyl]-14beta-estra-4,9-dien-3-one.

As another example for the rearrangement of a 14alpha-H steroid to the corresponding 14beta-H steroid, example 3 shows the production of 11beta-(4-acetylphenyl)-17alpha-hydroxy-17-(1-propinyl)-14beta-estra-4,9-dien-3-one and from example 4 it can be seen by the preparation of 11beta-(4-acetylphenyl)-17alpha-hydroxy-17-(2-propinyl)-14beta-estra-4,9-dien-3-one how the 2-propinyl function is introduced as C-17 side chain.

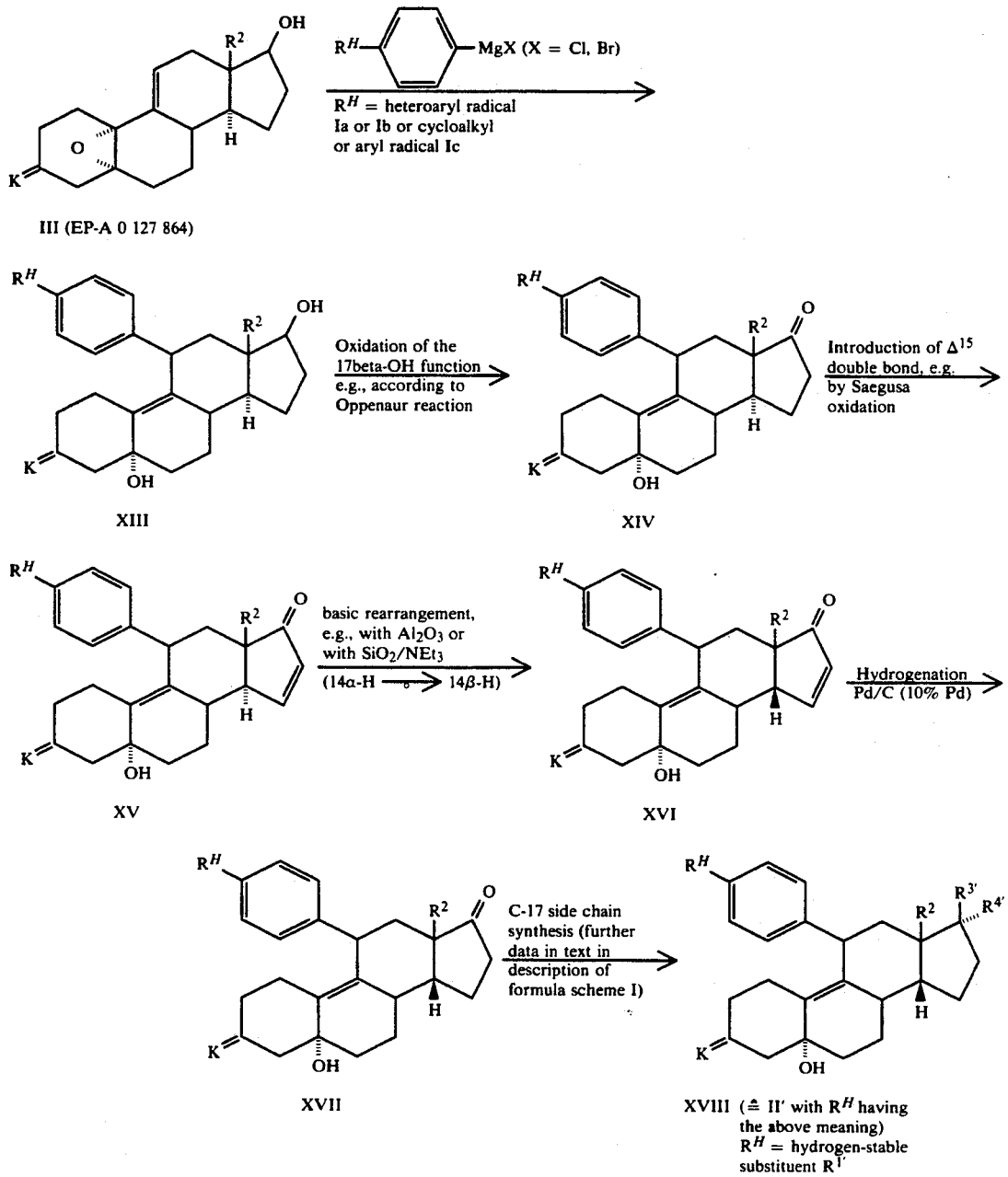

To reach the bridged initial compounds of formula II", it is equally possible—deviating from reaction scheme I—if the substituent standing for the radical R is hydrogenation-stable (i.e., if the latter exhibits no C—C multiple bonds), from a compound of formula IV"

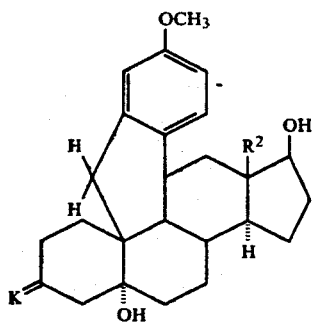
(IV''')

by cleavage of the O methyl group [Tetrahedron Lett. 1327, (1970)] to produce the free OH compound, to convert the latter with trifluoromethanesulfonic acid anhydride to the corresponding trifluoromethanesulfonate compound and then to functionalize the latter in a desired way as already indicated in the 4 position of the o-phenylene ring and only then to convert the 17-OH function, for example by Oppenauer oxidation to the 17-keto function. A compound of general formula V''' (cf. EP-A 0 283 428) thus obtained

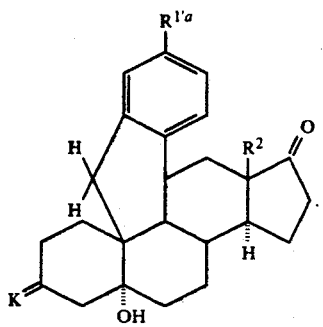
(V''')

in which $R^{1'a}$ stands for all substituents indicated under $R^{1'}$, with the exception of $OR^{III}$, $NR^{I}R^{II}$ and the hydrogenation unstable substituents contained in $R^{1'}$ [hydrogenation conditions: $H_2$ normal pressure, Pd/C (10% Pd)], as already indicated, by introduction of the $^{15}$double bond, basic rearrangement of the 14alpha-H into the 14beta-H compound and synthesis of the C-17 side chains, is converted to a compound of general formula $II'''^a$

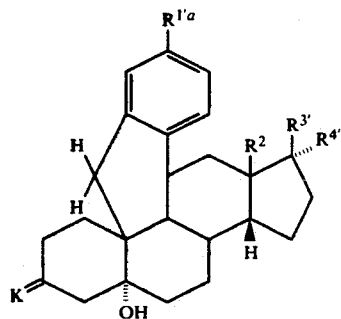
($II'''^a$)

The compounds of general formula I, with X meaning an oxygen atom, obtained after protecting group cleavage and dehydration, can optionally be converted, by reaction with hydroxylamine hydrochloride in the presence of tertiary amines at temperatures between −20° and +40° C., to the oximes (formula I with X meaning the hydroxyimino grouping N, OH, in which the hydroxy group can be syn or anti position). Suitable tertiary bases are, for example, trimethylamine, triethylamine, pyridine, N,N-dimethylaminopyridine, 1,5-diazabicyclo[4.3.0]nonene-5 (DBN) and 1,5-diazabicyclo[5.4.0]undecene-5 (DBU), and pyridine is preferred.

For removal of the 3-oxo group for an end product of general formula I with X meaning 2 hydrogen atoms, the directions indicated, e.g., in DOS 28 05 490 by thioketalization and then reductive cleavage can take place.

According to the invention it is also possible to functionalize the compounds of general formula I even further to compounds which, in comparison with those of formula I, then exhibit a modified B and/or A ring.

There can be mentioned compounds which on the C6 atom of the steroid skeleton carry a chlorine atom and/or a $C_1$-$C_4$ alkyl radical and/or on the C7 atom carry a $C_1$-$C_4$ alkyl radical, compounds which on the C6 atom carry two $C_1$-$C_4$ alkyl radicals and optionally on the C7 atom additionally carry a $C_1$-$C_4$ alkyl radical or else compounds which between the C6 and C7 atom exhibit a second bond and optionally on the C6 atom carry a chlorine atom or a $C_1$-$C_4$ alkyl radical.

It is also possible to replace both H atoms on the C6 atom of a compound of general formula I with a methylene or ethylene group, in which the C7 atom additionally can exhibit the above-mentioned substitution.

If L and M in general formula I together stand for a second bond between C3 and C4, additionally the A ring of the steroid skeleton can be modified. Then the C2 atom exhibits as substituent a hydrogen atom and a nitrile radical or a $C_1$-$C_4$ alkyl radical, a nitrile radical and a $C_1$-$C_4$ alkyl radical, two nitrile radicals, two $C_1$-$C_4$ alkyl radicals or a methylene or ethylene group and/or the C1 atom a $C_1$-$C_4$ alkyl radical.

Also compounds with a second bond between the C1 and the C2 atom or with a methylene bridge between the C1 and C2 atom, in which moreover in both cases optionally a nitrile radical or a $C_1$-$C_4$ alkyl radical is on the C2 atom, can be produced from compounds of general formula I optionally before or after modification of the B ring and belong to the object of this invention.

Finally, it is also possible to introduce in the 2 or 3 position a radical of the formula

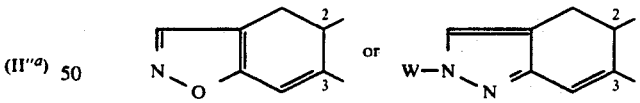

Introduction of 1,2 and 6,7 double bonds, besides the 3,4 double bond, can be performed according to known methods, for example, with dehydrogenation agents such as selenium(IV) oxide, chloranil, thallium triacetate or dichlorodicyanobenzoquinone (DDQ) or by allyl- or dieonolether bromation and then hydrogen bromide cleavage [J. Fried, J. A. Edwards, Organic Reactions in Steroid Chemistry, Van Nostrand Reinhold Company 1972, pp. 265-374, 1; Tetrahedron 42, (1986) 2971].

The allylbromation is performed, for example, with N-bromosuccinimide, N-bromoacetamide, 1,3-dibromo-5,5-dimethylhydantoin or dibromotetrachloroethane in the presence of a radical former such as dibenzoyl peroxide in a solvent. Aprotic solvents such as dioxane and chlorinated hydrocarbons such as, for example, carbon tetrachloride, chloroform or tetrachloroethylene are suitable as solvents. The reaction takes place between 0° C. and the boiling point of the solvent.

The dienoletherbromation is performed, for example, analogously to the directions in Steroids I, 233.

The hydrogen bromide cleavage with formation of the $\Delta^6$ double bond takes place by heating the 6-bromine compound with basis agents, preferably with lithium bromide and lithium carbonate or with lithium bromide and calcium carbonate in an aprotic solvent such as dimethylformamide at temperatures of 50° to 120° C. Another possibility of the HBr cleavage consists in the 6-bromine compound being heated in collidine or lutidine.

Starting from a saturated ring A, double bonds can be introduced in the 1,2 and 4,5 position at the same time, for example, by bromation to 2,4-dibromo-3-ketone and dehydrobromation of the dibromide with, for example, lithium or calcium carbonate and lithium bromide in dimethylformamide.

Introduction of a 6-methylene group can take place, for example, starting from a 3-amino-3(4),5(6)-diene derivative by reaction with formalin in alcoholic solution (Helv. Chim. Acta. 56 (1973) 2396) to the 6alpha-hydroxymethyl group and subsequent acid water cleavage, for example, with hydrochloric acid in dioxane/water or starting from a 3-alkoxy-3(4),5(6)-diene derivative, analogously to the method described in U.S. Pat. No. 4,544,555, or directly, starting from a 3-oxo-4(5)-ene derivative, analogously to the directions in Synthesis (1982) 34.

Methylenation of 6-methylene to the 6,6-ethylene compound takes place with dimethyl sulfoxonium methylide. For this purpose, the 6-methylene steroid is added to a suspension of trimethyl sulfoxonium iodide with sodium hydride in mineral oil and dimethyl sulfoxide or to a solution of trimethyl sulfoxonium iodide and sodium hydroxide in dimethyl sulfoxide. The reaction is ended after about 15 to 60 minutes at 20° to 40° C. [J. Am. Chem. Soc. 84 (1962) 866; European patent application 0150157].

Introduction of a 2-methylene group takes place analogously to the method of A. J. Manson and D. Woud [J. Org. Chem. 32 (1967) 3434] or the methods cited there.

The methylenation of the 2-methylene to the 2,2-ethylene compound takes place analogously to the methylenation of the 6-methylene compound [see also Chem. Ber. 98 (1965) 1470].

Mono- or di-alkylated compounds in the 2-position can be obtained, for example, analogously to the method of L. Nedelec, Tetrahedron 30 (1974) 3263.

Alkylated compounds in position 1 or 7 are obtained by 1,4- or 1,6-addition on the corresponding enones according to known methods [J. Fried, J. A. Edwards: Organic Reactions in Steroid Chemistry, Van Nostrand Reinhold Company 1972, pp. 75 to 82, 2; and J. Am. Chem. Soc. 99 (1977) 1673].

Alkylated compounds in position 6 can be obtained, for example, by opening of the corresponding 5alpha,-6alpha-epoxides and subsequent reactions (J. Fried, J. A. Edwards: Organic Reactions in Steroid Chemistry, Van Nostrand Reinhold Company 1972, pp. 82-66. 2).

1alpha,2alpha,6alpha,7alpha,6beta,7beta-Methylene compounds or a combination of the 1alpha,2alpha-methylene structure element with the two 6,7-methylene structure elements can be obtained by addition of diazomethane or dimethyl sulfoxonium methylide on the corresponding enones or by Simmons-Smith reaction [J. Fried, J. A. Edwards: Reactions in Steroid Chemistry, Van Nostrand Reinhold Company 1972, pp. 100–126; Rev. Soc. Quim. Soc. Mex. (1969) 171A; Chem. Ber. 101 (1968) 935; Chem. Ber. 99 (1966) 1118; Zeitschr. f. Naturf. 19b (1964) 944] of the corresponding allylalcohols.

Production of isoxazole ring annellated on positions 2 and 3 takes place by the synthesis of 2-hydroxymethylene compounds [Steroids 6 (1962) 178; J. Am. Chem. Soc. 83 (1961) 1478] and their reaction with hydroxylamine [J. Med. Chem. 6 (1963) 1].

[2,3-d]isoxazoles are also good starting materials for the synthesis of 2-cyano steroids [J. Med. Chem.6 (1963) 1].

Production of the pyrazole ring annellated on positions 2 and 3 takes place by reaction of 2-hydroxymethylene-3-oxo feedstocks with $R^{11}$ substituted hydrazine (U.S. Pat. No. 3,704,295).

Introduction of the chlorine or methyl substituent in C-6 of the steroid skeleton is performed, e.g., by the methods indicated in German laid-open specification 1 158 966 or in U.S. Pat. No. 4,544,555 and U.S. Pat. No. 4,196,203 by the corresponding 6,7-epoxides or 6-methylene derivatives as well as by oxidation of the 6-chloro-3,5,-dienol ether with dichlorodicyanobenzoquinone (DDQ) under acid conditions [Belgian patent 621,197 (1962)].

EXAMPLE 1

17-(3-Hydroxypropyl)-17alpha-hydroxy-11beta,19-(4-methoxy-o-phenylene)-14beta-androst-4-en-3-one (9)

a)

3,3-(2,2-Dimethyltrimethylenedioxy)-5alpha-hydroxy-11beta,19-(4-methoxy-o-phenylene)-14-androsten-17-one (4)

9.50 g of 11beta,19-(4-methoxy-o-phenylene)-5alpha-hydroxy-3,3-(2,2-dimethyltrimethylenedioxy)-androstan-17-one (1) (production of this initial compound is described following example 1) is instilled in a solution of 57.4 mmol of lithiumdiisopropylamide in 200 ml of absolute tetrahydrofuran, dissolved in 80 ml of absolute tetrahydrofuran, under protective gas at 0° C. Then chlorotrimethylsilane (13.8 ml) is instilled into the reaction mixture. After stirring for 30 more minutes, the reaction solution is poured onto ice-cold saturated sodium bicarbonate solution, the aqueous phase is extracted with ethyl acetate and the organic phase is washed with water and saturated ammonium chloride solution. After drying on sodium sulfate, the organic phase is concentrated by evaporation in a vacuum. 10.8 g of 3,3-(2,2-dimethyltrimethylenedioxy)-11beta,19-(4-methoxy-o-phenylene)-17-trimethylsilyloxy-16-androsten-5alpha-ol (2) is isolated crude as yellowish foam. This crude product is suspended in 127 ml of absolute acetonitrile and mixed with 6.4 g of palladium(II) acetate. After stirring for 12 more hours at room temperature, the reaction mixture is suctioned off over Celite, the filter residue is rewashed with ethyl acetate, the filtrate is concentrated by evaporation in a vacuum and the residue filtered over silica gel (grain size 0.2–0.5 mm). After concentrationo by evaporation of the filtrate, 7.1 g of 3,3-(2,2-dimethyltrimethylenedioxy)-5alpha-hydroxy-11beta,19-(4-methoxy-o-phenylene)-15-androsten-17-one (3) is obtained crude as yellowish foam. This crude product is dissolved in 2 l of a mixture of hexane/ethyl acetate (1:9), mixed with 100 ml of triethylamine and then stirred for 12 hours in the presence of 500 g of silica gel. After filtration, it is concentrated by evaporation and the residue is chromatographed on 800 g of silica gel with a mixture of hexane/ethyl acetate/triethylamine (80:19:1). There is obtained as the 1st fraction 3.47 g of above compound 4. $[\alpha]_D^{22}= +40.8°$ (C: 0.5, CHCl$_3$).

As 2nd fraction, 2.41 g of a mixture (1:1 according to TLC) was eluted from 3 and the above compound 4.

b)

3,3-(2,2-Dimethyltrimethylenedioxy)-5alpha-hydroxy-11beta,19-(4-methoxy-o-phenylene)-14beta-androstan-7-one (6)

Under protective gas, 6.22 ml of diisopropylamine in 200 ml of absolute tetrahydrofuran is taken at −10° C. and mixed with 30.5 ml of a 1.6M n-butyllithium solution (hexane). It is stirred for another 30 minutes at −5° C. and then 3.11 g of compound 4 prepared under a), dissolved in 60 ml of absolute tetrahydrofuran, is instilled. The reaction mixture is stirred for 15 minutes at −5° C. and then is mixed by instillation with 11.2 ml of trimethylchlorosilane. After 15 minutes, it is cooled to −70° C. and 5.4 ml of hydrogen fluoride-pyridine complex is instilled. Then the reaction mixture is stirred for 2 hours more at −60° C. and then poured onto saturated sodium bicarbonate solution. The aqueous phase is extracted with ethyl acetate, washed (NaCl solution), dried on sodium sulfate and concentrated by evaporation in a vacuum. 3.1 g of 3,3-(2,2-dimethyltrimethylenedioxy)-5alpha-hydroxy-11beta,19-(4-methoxy-o-phenylene)-14beta-androst-15-en-17-one (5) is obtained crude as yellowish foam. This crude product is dissolved in 200 ml of ethanol and hydroqenated with 369 mg of palladium/carbon (10% Pd). Filtration over Celite and removal of the solvent in a vacuum yields, after chromatography with hexane/ethyl acetate on silica gel, 2.18 g of above compound 6.
$[\alpha]_D^{22}= +55°$ (C: 0.51 CHCl$_3$)

c)

3,3-(2,2-Dimethyltrimethylenedioxy)-11beta,19-(4-methoxy-o-phenylene)-17-[3-(tetrahydropyran-2-yloxy)-1-propinyl]-14beta-androstane-5alpha,17alpha-diol (7)

The lithium organic compound is produced from 6.18 g of 3-(tetrahydropan-2-yloxy)-1-propine in 215 ml of absolute tetrahydrofuran and 27.5 ml of a 1.6M solution of n-butyllithium (hexane) at −10° C. and a solution of 2.18 g of compound 6 obtained under b) in 45 ml of absolute tetrahydrofuran is instilled in it at −10° C. It is first stirred for one hour at 0° C., then overnight at room temperature. It is poured into ice water and extracted with ethyl acetate. The crude product is chromatographed on neutral aluminum oxide with hexane/ethyl acetate. As main fraction 2.65 g of above compound 7 is obtained as white foam.

d)

3,3-(2,2-Dimethyltrimethylenedioxy)-11beta,19-(4-methoxy-o-phenylene)-17-[3-(tetrahydropyran-2-yloxy)-propyl]-14beta-androstane-5alpha,17alpha-diol (8)

2.53 g of above compound 8 is obtained, after hydrogenation, as described under b), from 2.65 g of compound 7, produced under c), in 150 ml of ethanol and 265 mg of palladium/carbon (10% Pd).

e 2.53 g of compound 8, produced under d), is dissolved in 125 ml of acetone and mixed with 6 ml of 4n hydrochloric acid. After stirring for 4 more hours at room temperature, the reaction mixture is poured onto saturated sodium bicarbonate solution and the aqueous phase is extracted with methylene chloride. The combined organic phases are dried on sodium sulfate and concentrated by evaporation in a vacuum. The residue is chromatographed on silica gel. 1.16 g of title compound 9 is obtained.
$[\alpha]_D^{22}= 82.6°$ (C: 0.5 CHCl$_3$).

f)

3,3-(2,2-Dimethyltrimethylenedioxy)-17-[3-(tetrahydropyran-2-yloxy)-propyl]-11beta,19-(4-trifluoromethylsulfonyloxy-o-phenylene)-14beta-androstane-5alpha,1-7alpha-diol (11)

2 g of methoxy compound 8 produced according to example 1d) is dissolved in 31 ml of absolute dimethylformamide and mixed with 658 m of sodium methane thiolate under protective gas. The reaction mixture is refluxed for 3 hours, then cooled to room temperature and then poured onto 200 ml of ice water. It is stirred at room temperature until the crude product flocculates as solid substance. Then it is suctioned off and dried in a vacuum. 1.90 of 3,3-(2,2-dimethyltrimethylenedioxy)-11beta,19-(4-hydroxy-o-phenylene)-17-[3-(tetrahydropyran-2-yloxy)-propyl]-14beta-androstane-5alpha,17alpha-diol (10) is obtained crude. This crude product is dissolved in 45 ml of absolute methylene chloride and mixed with 2.04 g of 4-dimethylaminopyridine. The solution is cooled to −70° C. under protective gas and slowly mixed, by instillation, with 0.7 ml of trifluoromethanesulfonic acid anhydride dissolved in 6 ml of absolute methylene chloride. After stirring for 1 more hour at −60° C. the reaction mixture is poured onto saturated sodium bicarbonate solution and the aqueous phase is extracted with methylene chloride. The combined organic phases are washed with saturated sodium chloride solution, dried on sodium sulfate and concentrated by evaporation in a vacuum. After chromatography of the residue on silica gel, 1.73 g of above compound 11 is obtained as yellowish foam.

IR (KBr): 1210 and 1420 cm$^{-1}$ of triflate.

Production of Initial Compound (1)

11beta,19 (4-Methoxy-o-phenylene)-5alpha-hydroxy-3,3-(2,2-dimethyltrimethylenedioxy)-androstan-17-one a)

19-(4-Methoxy-2-chlorophenyl)-3,3-(2,2-dimethyltrimethylenedioxy)-9(11)-androstene-5alpha,17beta-diol 5.4 g of magnesium chips in 45 ml of absolute diethyl ether under protective gas at room temperature is taken and mixed first with 0.55 ml of 2-chloro-5-methoxybenzylchloride and then carefully with 0.4 ml of 1,2-dibromoethane. After start of the reaction, then the remaining amount (19.4 ml) of the 2-chlorobenzylchloride, dissolved in 135 ml of absolute diethyl ether, is instilled over 40 minutes, without the internal temperature in the reaction vessel exceeding 30° C. After formation of the Grignard reagent is completed, the reaction mixture is cooled to 0° C. and 5alpha,10alpha-epoxy-3,3-(2,2-dimethyltrimethylenedioxy)- 9(11)-estren-17beta-ol (15 g), dissolved in 80 ml of absolute tetrahydrofuran, is slowly instilled. After stirring for one more hour at ice-bath temperature, the reaction mixture is slowly warmed overnight to room temperature and then poured onto diluted ammonium chloride solution. The aqueous phase is repeatedly extracted with ethyl acetate. The combined organic phases are washed neutral with sodium chloride solution, dried with sodium sulfate and concentrated by evaporation in a vacuum. The residue is chromatographed on aluminum oxide (neutral, stage III). 15.5 g of the above compound is obtained.

b)

11beta,19-(4-Methoxy-o-phenylene)-3,3-(2,2-dimethyl-trimethylenedioxy)-androstane-5alpha,17beta-diol 600 ml of anhydrous ammonia, with exclusion of moisture, is condensed in the reaction flask at −65° C. and mixed with 970 mg of freshly cut lithium chips. Immediately after the occurrence of the characteristic blue coloring, a solution of 15 g of the product obtained under a) in 450 ml of absolute tetrahydrofuran is instilled so that an interaction between discoloring of the reaction solution and blue coloring occurs. After the addition is completed, the excess lithium is eliminated by instillation of ethanol, most of the ammonia is removed by evaporation and the reaction mixture is poured onto water. The aqueous phase is extracted with ethyl acetate. The combined organic phases are then washed with sodium chloride solution, dried with sodium sulfate and concentrated by evaporation in a vacuum. 13.9 g of crude product is isolated. Chromatography on aluminum oxide (neutral, stage III) yields 11.6 g of the above compound.

$[\alpha]_D^{22} = +21.1°$ (CHCl$_3$); c=0.52)

Melting point: 223°-224° C. (diisopropyl ether)

c)

11beta,19-(4-Methoxy-o-phenylene)-5alpha-hydroxy-3,3-(2,2-dimethyltrimethylenedioxy)-androstan-17-one 14.2 g of chromium(III) oxide is added by portions to a mixture of 43.2 ml of pyridine and 384 ml of methylene chloride at 0° C. Then 11 g of the steroid obtained according to b), dissolved in 75 ml of methylene chloride, is slowly instilled at the same temperature into the reaction mixture and the latter is stirred for 2 more hours at ice-bath temperature. After the stirring is ended, the solid reaction components are allowed to settle, the supernatant phase is decanted and the precipitate is washed vigorously several times with methylene chloride. The combined organic phases are freed of the remaining organic components by washing with aqueous 0.5m potassium hydroxide solution, washed neutral with water, dried on sodium sulfate and concentrated by evaporation in a vacuum. 9 g of crude 11beta,19-(4-methoxy-o-phenylene)-5alpha-hydroxy-3,3-(2,2-dimethyltrimethylenedioxy)-androstan-17-one is isolated, whose purity is sufficient for further reactions. 500 mg is purified by chromatography on aluminum oxide (neutral, stage III) for analytical purposes. 443 mg of the desired product is isolated as white foam.

$[\alpha]_D^{22} = +33°$ (CHCl$_3$; c=0.55)

Melting point: 235°-238° C.

EXAMPLE 2

17alpha-Hydroxy-17-(1-propinyl)-11beta-[4-(2-thiazolyl)-phenyl]-4beta-estra-4,9-dien-3-one (28)

a)

3,3(2,2-Dimethyltrimethylenedioxy)-11beta-[4-(2-thiazolyl)phenyl]-9-estrene-5alpha,17beta-diol (21)

13.4 g of magnesium chips under protective gas in 200 ml of absolute tetrahydrofuran is taken and mixed with 3.5 ml of dibromoethane at 50° C. After the reaction is completed, a solution of 97.8 g of 1-(chloro-4-(2-thiazolyl)-benzene (preparation according to literature: Tetrahedron Letters 27, 4407 (1986)]in 250 ml of absolute tetrahydrofuran is slowly instilled. It is stirred for 4 more hours at 70° C. After the reaction is completed, the Grignard solution is cooled to 0° C. and mixed with 1.43 g of copper(I) chloride. After 30 minutes, a solution of 37.4 g of 5alpha,10alpha-epoxy-3,3-(2,2-dimethyltrimethylenedioxy)-9(11)-estren-17-ol (EP-A 0 127 864) in 300 ml of absolute tetrahydrofuran is instilled. After addition, the reaction mixture is stirred for 30 minutes more at 0° C. and 15 minutes at room temperature and then poured onto ice water. The aqueous phase is extracted with ethyl acetate, the organic phases are combined and washed with saturated sodium chloride solution. After drying on sodium sulfate and concentration by evaporation in a vacuum, the resulting residue is chromatographed on aluminum oxide with a mixture of ethyl acetate/hexane. 40.1 g of above compound 21 is obtained.

b)

3,3-(2,2-Dimethyltrimethylenedioxy)-5alpha-hydroxy-11beta-[4-(2-thizolyl)-phenyl]-9-estren-17-one (22)

40.1 g of compound 21 produced under 2a is dissolved in 650 ml of toluene, mixed with 20.1 g of aluminum isopropylate and 140 ml of cyclohexanone and refluxed for 2 hours on a water separator. It is allowed to cool, about 400 ml of saturated sodium bicarbonate solution is instilled, and it is suctioned off over Celite. The filtrate is washed (NaCl solution), dried and concentrated by evaporation in a vacuum. The resulting residue is chromatographed on aluminum oxide with a mixture of ethyl acetate/hexane. 25.9 g of above compound 22 is obtained.

c)

3,3-(2,2-Dimethyltrimethylenedioxy)-5alpha-hydroxy-11beta-[4-(2-thiazolyl)-phenyl)-9-15-estradien-17-one (24)

Analogously to example 1a), 29.3 g of 3,3-(2,2-dimethyltrimethylenedioxy)-11beta-[4-(2-thiazolyl)-phenyl]-17-trimethylsilyloxy-9,16-estradien-5alpha-ol (23) is obtained crude as yellowish foam from 25.9 g of compound 22 produced under 2b, 145 mmol of lithiumdiisopropylamide and 34.8 ml of chlorotrimethylsilane. This crude product is suspended in 250 ml of absolute acetonitrile and mixed with 15.0 g of palladium(II) acetate. Working up takes place as described in example 1a). 21.g of above compound 24 is isolated as crude product.

d)

3,3-(2,2-Dimethyltrimethylenedioxy)-5alpha-hydroxy-11beta-[4-(2-thiazolyl)-phenyl]-14beta-estra-9,15-dien-17-one (25)

21.1 g of compound 24 produced under example 2c, dissolved in 2.0 l of ethyl acetate, is mixed with 140 ml of triethylamine and stirred for 24 hours in the presence of 950 g of silica gel. After filtration, it is concentrated by evaporation in a vacuum and the residue is chromatographed on 2 kg of silica gel with a mixture of hexane/ethyl acetate/triethylamine (80:19:1). 13.1 g of above compound 25 is obtained.

e)
3,3-(2,2-Dimethyltrimethylenedioxy)-5alpha-hydroxy-11beta-[4-(2-thiazolyl)-phenyl]-14beta-estr-9-en-17-one (26)

A solution of 13.1 g of the compound produced under example 2d) in 450 ml of ethanol is hydrogenated with 1.3 g of palladium/carbon (10% Pd). Filtration over Celite and removal of the solvent in a vacuum yields, after chromatography with hexane/ethyl acetate on aluminum oxide 9.3 g of above compound 26.

f)
3,3-(2,2-Dimethyltrimethylenedioxy)-17beta-(1-propinyl)-11beta-[4-(2-thiazolyl)-phenyl]-14beta-estr-9-ene-5alpha,17alpha-diol (27)

200 ml of absolute tetrahydrofuran is saturated by 30 minutes introduction of methylacetylene at 0° C. Then 28.5 ml of a 1.6M solution of n-butyllithium in hexane is instilled at 0° to 5° C., it is stirred for 15 more minutes after the addition and then a solution of 1.23 g of the compound produced under example 2e) in 2o ml of absolute tetrahydrofuran is instilled. The reaction mixture is stirred for 1 more hour after the addition is completed, is poured onto ice water and the aqueous phase is extracted with ethyl acetate. The combined organic phases are dried on sodium sulfate and concentrated by evaporation in a vacuum. The residue is chromatographed on aluminum oxide with a mixture of ethyl acetate/hexane. 823 mg of above compound 27 is obtained.

g 823 mg of the compound produced under example 2f) is dissolved in 13 ml of 70% aqueous acetic acid and stirred for 1 hour at 50° C. under protective gas. After cooling, it is poured in ice water, neutralized by addition of saturated sodium bicarbonate solution and extracted with ethyl acetate. The combined organic phases are dried on sodium sulfate and concentrated by evaporation in a vacuum. The residue is chromatographed with a mixture of hexane/ethyl acetate on silica gel. 310 mg of title compound 28 is isolated as white foam.

$^1$H-NMR (CDCl$_3$)=Py.d$_5$) $\delta$: 0.91 (s; 3H, H—CH$_3$), 1.89 (s; 3H, H—CH$_3$), 4.5 (m; 1H, 11-H), 5.69 (s; 1H, 4-H), 7.30; 7.80 (in each case d, J=3Hz; 2H, —S—CH=CH—N) 7.50; 7.75 (AA'BB' system, J=9Hz; HH, arH)

EXAMPLE 3

11beta-(4-Acetylphenyl)-17alpha-hydroxy-17(1-propinyl)-14beta-estra-4,9-dien-3-one 750 mg of 11beta-{4-[1,1-(2,2-dimethyltrimethylenedioxy)ethyl]-phenyl}- 3,3-(2,2-dimethyltrimethylenedioxy)-17beta-(1-propinyl)-14beta-estr-9-ene-5alpha,17alpha-diol is dissolved in 12 ml of 70% aqueous acetic acid and stirred for 1 hour at 50° C. under protective gas. After cooling, it is poured into ice water, neutralized by addition of saturated sodium bicarbonate solution and extracted with ethyl acetate. The combined organic phases are dried on sodium sulfate and concentrated by evaporation in a vacuum. The residue is chromatographed with a mixture of hexane/ethyl acetate on silica gel. 300 mg of the title compound is isolated as white foam.

$[\alpha]_D^{22}=242°$ (CHCl$_3$; c=0.500).

Production of the initial material takes place as follows:

a) Under protective gas, 10 ml of diisopropylamine in 290 ml of absolute tetrahydrofuran at −10° C. is taken and mixed with 50 ml of a 1.6m n-butyllithium solution (hexane). It is stirred for a half hour more at 0° C., then again cooled to −10° C. and 13.6 g of 11beta-{4-[1,1-(2,2-dimethyltrimethylenedioxy)-ethyl]phenyl }5alpha-hydroxy-3,3-(2,2-dimethyltrimethylenedioxy)-9-estren-17-one (production according to European patent application 86101548.5, publication No. 190759, example 6), dissolved in 150 ml of absolute tetrahydrofuran is instilled. After the addition is completed, it is stirred for 15 more minutes and then 17.2 ml of trimethylchlorosilane is instilled. Then the reaction mixture is poured onto ice-cold saturated sodium bicarbonate solution and the aqueous phase is extracted with ethyl acetate. The combined organic phases are washed several times with saturated ammonium chloride solution and concentrated by evaporation in a vacuum. The residue is crystallized from 50 ml of acetonitrile. 13.2 g of 17-trimethylsilyloxy-11beta-{4-[1,1-(2,2-dimethyltrimethylenedioxy)-ethyl]-phenyl}3,3-(2,2-dimethyltrimethylenedioxy)-9,16-estradien-5alpha-ol is obtained.

b) 4.27 g of palladium(II) acetate in 150 ml of absolute acetonitrile is taken and mixed with 12.12 g of the compound produced under a). The reaction mixture is stirred for 16 hours at room temperature, then filtered on silica gel and the filter residue is mixed well with methylene chloride. The organic phase is concentrated by evaporation in a vacuum and the residue chromatographed on silica gel. 10 g of 11beta-{4-[1,1-(2,2-dimethyltrimethylenedioxy)-ethyl]-phenyl}5alpha-hydroxy-3,3-(2,2-dimethyltrimethylenedioxy)-9,15-estradien-17-one is isolated as white foam.

c) 17.3 g of 11beta-{4-[1,1-(2,2-dimethyltrimethylenedioxy)ethyl]-phenyl}-3,3-(2,2-dimethyltrimethylenedioxy)-5alpha-hydroxy-estra-9,15-dien-17-one, dissolved in 1.73 l of ethyl acetate, is mixed with 120 ml of triethylamine and stirred for 24 hours in the presence of 800 g of silica gel. After filtration, it is concentrated by evaporation in a vacuum and the residue is chromatographed on 1.73 kg of silica gel with a mixture of hexane/ethyl acetate/triethylamine (49:49:2). 10.4 g of 11beta-{4-[1,1-(2,2-dimethyltrimethylenedioxy)-ethyl]-phenyl}-3,3-(2,2-dimethyltrimethylenedioxy)-5alpha-hydroxy-14-beta-estra-9,15-dien-17-one is obtained.

d) A solution of 3.0 g of the compound produced under 3c) in 150 ml of ethanol is hydrogenated with 300 mg of palladium/carbon (10% Pd). Filtration over Celite and removal of the solvent in a vacuum yields, after chromatography with hexane/ethyl acetate on aluminum oxide 2.34 g of 11beta-{4-[1,1-(2,2-dimethyltrimethylenedioxy)-ethyl]-phenyl}-3,3-(2,2 -dimethyltrimethylenedioxy)-5alpha-hydroxy-14beta-estr-9-en-17-one.

Melting point: 145°-148° C.

e) 200 ml of absolute tetrahydrofuran is saturated by 30 minutes introduction of methylacetylene at 0° C. Then 28.5 ml of a 1.6M solution of n-butyllithium in hexane is instilled 0° C. to 5° C., stirred for 15 more minutes after addition and then a solution of 1.32 g of the compound produced under 3d) in 20 ml of absolute tetrahydrofuran is instilled. The reaction mixture is stirred for 60 minutes more after the addition, is poured onto ice water and the aqueous phase is extracted with ethyl acetate. The combined organic phases were dried on sodium sulfate and concentrated by evaporation in a vacuum. The residue is chromatographed on aluminum oxide (neutral, stage III) with a mixture of ethyl acetate/hexane. 800 mg of 11beta-{4-[1,1-(2,2-dimethyltrimethylenedioxy)-ethyl]-phenyl}-3,3-(2,2-dimethyltrimethylenedioxy)-17beta(1-propinyl)-14beta-estr-9-ene-5alpha,17alpha-diol is obtained.

$^1$H-NMR(CD$_2$Cl$_2$) δ: 0.57 (s; 3H. H-CH$_3$), 0.81 (s; 3H, H—CH$_3$), 0.90 (s; 3H, H—CH$_3$), 0.99 (s; 3H, 18-H), 1.22 (s: 3H, H—CH$_3$), 1,48 (s: 3H, H—CH$_3$), 1.91 (s: 3H, H—CH$_3$).

EXAMPLE 4

11beta-(4-Acetylphenyl)-17alpha-hydroxy-17-(2-propinyl)14beta-estra-4,9-dien-3-one 470 mg of 11beta-(4-Acetylphenyl)-17alpha-hydroxy-17-(3-trimethysilyl-2-propinyl)-14beta-estra-4,9-dien-3-one in 24 ml of tetrahydrofuran is mixed with 2.35 ml of a 1M solution of tetrabutylammonium fluoride in tetrahydrofuran and stirred for 5 minutes at room temperature. It is poured on water and extracted with ethyl acetate. The combined organic phases are washed with water, dried on sodium sulfate and concentrated by evaporation. The residue is chromatographed with a mixture of hexane/ethyl acetate on silica gel. 280 mg of the title compound is isolated as foam.

$[\alpha]_D^{22} = 166°$ (CHCl$_3$: c=0.500).

Production of the initial material takes place as follows:

a) 13.6 ml of a 1.6M solution of n-butyllithium in hexane is instilled in a solution of 2.33 g of 1-(trimethylsilyl)-1-propine in 100 ml of absolute tetrahydrofuran at −5° C. After addition, it is stirred for 1 hour at this temperature, cooled to −78° C. and then a solution of 1.20 g of the compound prepared under 3d) in 13 ml of tetrahydrofuran is instilled. The reaction mixture is continued to be stirred overnight at room temperature, poured onto ice water and the aqueous phase is extracted with ethyl acetate. The combined organic phases are dried on sodium sulfate and concentrated by evaporation. The residue is chromatographed with a mixture of hexane/ethyl acetate on silica gel. 940 mg of 11beta-{4-[1,1-(2,2-dimethyltrimethylenedioxy)ethyl]-phenyl}-3,3-(2,2-dimethyltrimethylenedioxy)-17-(3-trimethylsilyl-2-propinyl)-14beta-estr-9-ene-5alpha,17alpha-diol is obtained as foam.

b) As described under example 3, 486 mg of 11beta-(4-acetylphenyl)-17alpha-hydroxy-(3-trimethylsilyl-2-propinyl)-14beta-estra-4,9-dien-3-one is obtained from 940 mg of the compound produced under 4a) and 13 ml of 70% aqueous acetic acid.

$[\alpha]_D^{22} = 150°$ (CHCl3; c=0.500).

General Instructions 1 for the Production of the Compounds of General Formula I" by Acid Cleavage of the Compounds of General Formula II (Table 1)

A solution of x g of steroid in y ml of acetone is mixed with z ml of 4N hydrochloric acid and stirred a minutes at t°C under argon. Then it is poured on saturated sodium bicarbonate solution and extracted with methylene chloride. The combined organic phases are washed with saturated sodium chloride solution, dried on sodium sulfate and concentrated by evaporation in a vacuum. By chromatography on silica gel with a mixture of ethyl acetate/hexane, b g of the desired compound of general formula I' is obtained from the crude product.

General Instructions 2 for the Production of the Compounds of General Formula I' by Acid Cleavage of the Compounds of General Formula II (Table 2)

A solution of x g of steroid in y ml of 70% acetic acid is stirred for z minutes at t°C. Then it is poured on ice water, neutralized by addition of aqueous ammonia solution and extracted with methylene chloride. Analogously to the above working up, a g of the desired compound of general formula I' is obtained.

EXAMPLE 5

17alpha-Hydroxy-17-(3-hydroxypropyl)-11beta,19-[4-vinyl-o-phenylene]-14beta-androst-4-en-3-one (32) (Table 1)

a)

3,3-(2,2-Dimethyltrimethylenedioxy)-17-[3-tetrahydropryan-2-yloxy)-propyl]-11beta,19-(4-tri-n-butylstannyl-o-phenylene)-14beta-androstane-5alpha,17alpha-diol (29)

4.62 g of 3,3(2,2-dimethyltrimethylenedioxy)-17-[3-(tetrahydropyran-2-yloxy)-propyl]-11beta,19-(4-trifluoromethylsulfonyloxy-o-phenylene)-14beta-androstane-5alpha,17alpha-diol (compound 11, example 1f) is taken under protective gas in 160 ml of absolute dioxane, mixed with 9.7 ml of hexabutylditin, 290 mg of tetrakis-(triphenylphosphine)palladium(O) and 810 mg of lithium chloride and then refluxed for 30 minutes. After filtration over Celite it is concentrated by evaporation in a vacuum and the residue is chromatographed on aluminum oxide with a mixture of ethyl acetate/hexane. 5.7 g of the above compound is obtained.

b)

3,3-(2,2-dimethyltrimethylenedioxy)-17-[3-(tetrahydropyran-2-yloxy)-propyl]-11beta,19-(4-iodo-o-phenylene)-14beta-androstane-5alpha,17alpha-diol (30)

3.2 g of the compound produced under a) is dissolved in 80 ml of methylene chloride and mixed by portions with 905 mg of iodine crystals at 0° C. under argon. After 30 minutes, the reaction mixture is washed with saturated sodium thiosulfate and saturated sodium chloride solution. After drying on sodium sulfate, concentration by evaporation in a vacuum and column chromatographic purification on aluminum oxide, 1.9 g of the above compound is obtained.

c)

3,3(2,2-Dimethyltrimethylenedioxy)-17-[3-(tetrahydropyran-2-yloxy)-propyl]-11beta,19-(4-vinyl-o-phenylene)-14beta-androstane-5alpha,17alpha-diol (31)

Variant 1

1.9 g of the compound produced under b) under protective gas in 80 ml of absolute toluene is taken, mixed with 1.03 g of tributylvinyltin and 298 mg of tetrakis-(triphenylphosphine)palladium(O) and refluxed for 30 minutes. After concentration by evaporation in a vacuum and purification on silica gel, 480 mg of the above compound is obtained.

Variant 2

0.99 g of 3,3(2,2-dimethyltrimethylenedioxy)-17-[3-(tetrahydropyran-2-yloxy)-propyl]-11beta,19-(4-trifluoromethylsulfonyloxy-o-phenylene)-14beta-androstane-5alpha,17alpha-diol (11) is taken under protective gas in 20 ml of absolute dimethylformamide, mixed with 0.54 g of tributylvinyltin, 158 mg of tetrakis-(triphenylphosphine)palladium(O) and 113 mg of lithium chloride and refluxed for 30 minutes. After concentration by evaporation in a vacuum and purification on silica gel, 640 mg of the above compound is obtained.

d

Title compound 32 is obtained according to the general instructions 1 (Table 1).

EXAMPLE 6

17alpha-Hydroxy-17-(3-hydroxypropyl)-11beta,19-(4-ethyl-o-phenylene)-14beta-androst-4-en-3-one (34) (Table 1)

a)

3,3(2,2-Dimethyltrimethylenedioxy)-17-[3-(tetrahydropyran-2-yloxy)-propyl]-11beta,19-(4-ethyl-o-phenylene)-14beta-androstane-5alpha,17alpha-diol (33)

640 mg of the compound produced under example 5c) in 50 ml of absolute tetrahydrofuran is hydrogenated under normal pressure after addition of 140 mg of palladium/CaCO$_3$ (5% Pd). After filtration over Celite and column chromatographic purification on silica gel, 550 mg of above compound 33 is isolated.

b

Title compound 34 is obtained according to general instructions 1 (Table 1).

EXAMPLE 7

17alpha-Hydroxy-17-(3-hydroxypropyl)-11beta,19-[4-(3-pyridyl)-o-phenylene]-14beta-androst-4-en-3-one (36) (Table 1)

a)

3,3(2,2-Dimethyltrimethylenedioxy)-17-[3-(tetrahydropyran-2-yloxy)-propyl]-11beta,19-[4-(3-pyridyl)-o-phenylene]-14beta-androstane-5alpha,17alpha-diol (35)

1.65 g of the compound produced under example 5a) is taken under protective gas in 45 ml of absolute toluene, mixed with 2.9 g of 3-bromopyridine and 212 mg of tetrakis-(triphenylphosphine)palladium(O) and refluxed for 15 hours. After concentration by evaporation in a vacuum and purification on silica gel, 800 mg of the above compound is obtained.

b

Title compound 36 is obtained according to the general instructions 1.

EXAMPLE 8

17alpha-Hydroxy-17-(3-hydroxypropyl)-11beta,19-[4-(3-thienyl)-o-phenylene]-14beta-androst-4-en-3-one (38) (Table 1)

a)

3,3(2,2-Dimethyltrimethylenedioxy)-17-[3-(tetrahydropyran-2-yloxy)-propyl]-11beta,19-[4-(3-furyl)-o-phenylene]- 14beta-androstane-5alpha,17alpha-diol (37)

1.74 g of the compound produced under example 5a) is taken under protective gas in 40 ml of absolute toluene, mixed with 3.15 g of 3-bromothiophene and 224 mg of tetrakis(triphenylphosphine)palladium(O) and refluxed for 15 hours. After concentration by evaporation in a vacuum and purification on silica gel, 720 mg of the above compound is obtained.

b

Title compound 38 is obtained according to the general instructions 1.

EXAMPLE 9

17alpha-Hydroxy-17-(3-hydroxypropyl)-11beta,19-(4-dimethylamino-o-phenylene)-14beta-androst-4-en-3-one (51) (Table 1)

a)

3,3(2,2-Dimethyltrimethylenedioxy)-5alpha-hydroxy-11beta,19-(4-dimethylamino-o-phenylene)-14beta-androsten-17-one (45)

18.6 g of 11beta,19-(4-dimethylamino-o-phenylene)-5alpha-hydroxy-3,3(2,2-dimethyltrimethylenedioxy)-androstan-17-one (42) (production of this initial compound is described following example 9) is instilled in a solution of 109.4 mmol of lithium diisopropylamide in 450 ml of absolute tetrahydrofuran, dissolved in 150 ml of tetrahydrofuran, under protective gas at 0° C. Then chlorotrimethylsilane (26.4 ml) is instilled in the reaction mixture. After stirring for 30 more minutes, the reaction solution is poured onto ice-cold saturated sodium bicarbonate solution, the aqueous phase is extracted with ethyl acetate and the organic phase is washed with water and saturated ammonium chloride solution. After drying on sodium sulfate, the organic phase is concentrated by evaporation in a vacuum. 20.1 g of 3,3(2,2-dimethyltrimethylenedioxy)-11beta,19-(4-dimethylamino-o-phenylene)-17-trimethylsilyloxy-16-androsten-5alpha-ol (43) is isolated crude as yellowish foam. This crude product is suspended in 250 ml of absolute acetonitrile and mixed with 11.6 g of palladium(II) acetate. After stirring for 12 more hours at room temperature, the reaction mixture is suctioned off over Celite, the filter residue is rewashed with ethyl acetate, the filtrate is concentrated by evaporation in a vacuum and the residue is filtered over silica gel (grain size 0.2–0.5 mm). After concentration of the filtrate by evaporation, 7.0 g of 3,3(2,2-dimethyltrimethylenedioxy)-5alpha-hydroxy-11beta, 19-(4-dimethylamino-o-phenylene)-15-androsten-17-one (44) is obtained crude as yellowish foam. This crude product is dissolved in 1 liter of a mixture of hexane/ethyl acetate (1:9), mixed with 72 ml of triethylamine and stirred for 72 hours in the presence of 400 g of silica gel. After filtration, it is concentrated by evaporation and the residue is chromatographed on 800 g of silica gel with a mixture of hexane/ethyl acetate/triethylamine (80:19:1). 5.36 g of above compound 45 is obtained as a 1st fraction. 0.93 g of a mixture (3:1, according to TLC) of 44 and above compound 45 is eluted as 2nd fraction.

b)

3,3(2,2-Dimethyltrimethylenedioxy)-5alpha-hydroxy-11beta,19-(4-dimethylamino-o-phenylene)-14beta-androstan-17-one (47)

6.01 ml of diisopropylamine in 180 ml of absolute tetrahydrofuran is taken under protective gas at −10° C. and is mixed with 29.5 ml of a 1.6M n-butyllithium solution (hexane). It is stirred for 30 more minutes at −5° C. and then 3.1 g of compound 45, produced under a), dissolved in 50 ml of absolute tetrahydrofuran, is instilled. The reaction mixture is stirred for 15 more minutes at −5° C. and then mixed by instillation with 10.0 ml of trimethylchlorosilane. After 15 minutes it is cooled to −70° C. and 5.2 ml of hydrogen fluoride-pyridine complex is instilled. Then the reaction mixture is stirred for 10 more hours at −30° C. and then poured onto saturated sodium bicarbonate solution. The aqueous phase is extracted with ethyl acetate, washed (NaCl solution), dried on sodium sulfate and concentrated by evaporation in a vacuum. 3.0 g of 3,3(2,2-dimethyl-trimethylenedioxy)-5alpha-hydroxy-11beta,19-(4-dimethylamino-o-phenylene)-14beta-androst-4-en-17-one (46) is obtained crude as yellowish foam. This crude product is dissolved in 120 ml of tetrahydrofuran/ethanol (1:1) and hydrogenated with 500 mg of palladium/calcium carbonate (5% Pd). Filtration over Celite and removal of the solvent in a vacuum yields, after chromatography with hexane/ethyl acetate on silica gel, 2.4 g of above compound 47.

c)
3,3(2,2-Dimethyltrimethylenedioxy)-11beta,19-(4-dimethylamino-o-phenylene)-17-[3-(tetrahydropyran-2-yloxy)-1propinyl]-14beta-androstane-5alpha,17alpha-diol (48)

The lithium organic compound is produced from 9.94 g of 3-(tetrahydropyran-2-yloxy)-1-propine in 170 ml of absolute tetrahydrofuran and 45.0 ml of a 1.6M solution of n-butyllithium (hexane) at −10° C. and a solution of 2.40 g of compound 47 obtained under b) in 45 ml of absolute tetrahydrofuran is instilled therein at −10° C. It is stirred first for 1 hour at 0° C., then overnight at room temperature. It is poured into ice water and extracted with ethyl acetate. The crude product is chromatographed on neutral aluminum oxide with hexane/ethyl acetate. As main fraction 2.14 g of above compound 48 is obtained as white foam.

d)
3,3(2,2-Dimethyltrimethylenedioxy)-11beta,19-(4-dimethylamino-o-phenylene)-17-[3-(tetrahydropyran 2-yloxy)propyl]-14beta-androstane-5alpha,17alpha-diol (49)

As described under b), 1.79 g of above compound 49 is obtained, after hydrogenation, from 2.14 g of compound 48, produced under c), in 140 ml of ethanol/tetrahydrofuran (1:1) and 430 mg of palladium/calcium carbonate (5% Pd).

e)
17-(3-Hydroxypropyl)-17alpha,5alpha-dihydroxy-11beta,19-(4-dimethylamino-o-phenylene)-14beta-androst-4-en-3-one (50)

1.77 g of compound 49 produced under d), is dissolved in 90 ml of acetone and mixed with 4.4 ml of 4N hydrochloric acid. After stirring for 16 hours at 0° C., the reaction mixture is poured onto saturated sodium bicarbonate solution and the aqueous phase is extracted with methylene chloride. The combined organic phases are dried on sodium sulfate and concentrated by evaporation in a vacuum. The residue is chromatographed on silica gel. 0.98 g of above compound 50 is obtained.

$^1$H-NMR (CDCl$_3$) δ:0.55 (3H,s,18-H); 2.93(6H,s,NMe$_2$); 3.68(2H,m,CH$_2$OH); 6.4–7.3(3H,3m, protons on the aromatic substance)

f 0.98 g of compound 50 produced under e) is dissolved in 50 ml of acetone and mixed with 2.5 ml of 4N hydrochloric acid. After stirring for 4 more hours at 25° C., it is worked up as described under e). 0.67 g of title compound 51 is obtained.

Production of Initial Compound (42)

11beta,19-(4-Dimethylamino-o-phenylene)-5alpha-hydroxy-3,3(2,2-dimethyltrimethylenedioxy)-androstan-17-one a)
19-(4-Dimethylamino-2-chlorophenyl)-3,3(2,2-dimethyl-yl-trimethylenedioxy)-9(11)-androstene-5alpha,17beta-diol (40)

7.72 g of magnesium chips are taken at room temperature under protective gas in 50 ml of absolute diethyl ether and mixed with 0.7 ml of 1,2-dibromoethane. After the start of the reaction, 64.5 g of 2-chloro-5-dimethylamino-benzylchloride, dissolved in 700 ml of absolute diethyl ether, is then instilled over 40 minutes without the internal temperature in the reaction vessel exceeding 30° C. After the formation of the Grignard reagent is completed, 5alpha,10alpha-epoxy-3,3(2,2-dimethyltrimethylenedioxy)-9(11)-estren-17beta-ol (23.6 g), dissolved in 200 ml of absolute tetrahydrofuran, is slowly instilled. After stirring for 1 more hour at ice-bath temperature, it is stirred overnight and then poured onto dilute ammonium chloride solution. The aqueous phase is extracted several times with ethyl acetate. The combined organic phases are washed neutral with sodium chloride solution, dried with sodium sulfate and concentrated by evaporation in a vacuum. The residue is chromatographed on aluminum oxide (neutral, step III). 33.0 g of the above compound is obtained.

b)
11beta,19-(4-Dimethylamino-o-phenylene)-3,3(2,2-dimethyltrimethylenedioxy)-androstane-5alpha,17beta-diol (41)

790 ml of anhydrous ammonia, with exclusion of moisture, is condensed in the reaction vessel at −65° C. and mixed with 2.91 g of freshly cut lithium chips. Immediately after occurrence of the characteristic blue coloring, a solution of 33 g of the product obtained under a) in 2000 ml of absolute tetrahydrofuran is instilled so that an interaction between discoloring of the reaction solution and blue coloring occurs. After the addition is completed, the excess lithium is eliminated by instillation of ethanol, most of the ammonia is removed by evaporation and the reaction mixture is poured onto water. The aqueous phase is extracted with ethyl acetate. The combined organic phases are then washed with sodium chloride solution, dried with sodium sulfate and concentrated by evaporation in a vacuum. 31.5 g of crude product is isolated. Chromatography on silica gel yields 20.0 g of the above compound.

c)
11beta,19-(4-Dimethylamino-o-phenylene)-5alpha-hydroxy-3,3(2,2-dimethyltrimethylenedioxy)-androstan-17-one (42)

20.3 g of aluminum-tri-isopropanolate and 147 ml of cyclohexanone are added to 25.1 g of the compound produced under b) in 1000 ml of toluene. It is refluxed for 1.5 hours and about 250 ml is continuously distilled off. The reaction mixture is mixed with saturated sodium bicarbonate solution, suctioned off through Celite, washed neutral (sodium chloride solution) and concentrated by evaporation. Chromatography on aluminum oxide with hexane/ethyl acetate yields 18.6 g of initial product 42.

EXAMPLE 10

11beta,19-(4-Dimethylamino-o-phenylene)-4',5'-dihydrospiro[14beta-androst-4-ene-17alpha,2'-(3'H)-furan-3-one (52)

404 mg of compound 51 produced under example 9) is dissolved in 20 ml of methylene chloride and mixed with 1.2 ml of triethylamine. The mixture is cooled to 0° C. and 500 mg of p-toluenesulfonic acid chloride is added. After 60 minutes at 0° C. and refluxing for another 6 hours, the reaction mixture is poured onto saturated sodium bicarbonate solution, the aqueous phase is extracted with methylene chloride, the combined organic phases are washed with saturated sodium chloride solution, dried (sodium sulfate) and concentrated by evaporation in a vacuum. After chromatography of the crude product on silica gel, 370 mg of title compound 52 is isolated.

$[\alpha]_D^{22} = 124.0°$ (CHCl$_3$; c=0.515)

EXAMPLE 11

11beta,19-(4-dimethylamino-o-phenylene)-17alpha-hydroxy-17(3-hydroxy-propyl)-14beta-androsta-I,4-dien-3-one (55)

a)

11beta,19-(4-Dimethylamino-o-phenylene)-17alpha-trimethylsilyloxy-17-(3-trimethylsilyloxypropyl)-3-trimethylsilyloxy-14beta-androsta-2,4-diene (53)

1.5 g of compound 51 prepared according to example 9f), dissolved in 45 ml of absolute tetrahydrofuran, is instilled in a solution of 33 mmol of lithium diisopropylamide in 150 ml of absolute tetrahydrofuran under argon at 0° C. Then, trimethylchlorosilane (7.95 ml) is instilled in the reaction mixture. After stirring for 45 minutes, the reaction solution is poured onto cold saturated sodium bicarbonate solution, the aqueous phase is extracted with ethyl acetate and the organic phase is successively washed with water and saturated ammonium chloride solution. After drying on sodium sulfate, it is concentrated by evaporation in a vacuum. 2.48 g of the silyldienol ether 53 is obtained as crude product.

b)

11beta,19-(4-Dimethylamino-o-phenylene)-17alpha-trimethylsilyloxy-17-(3-trimethylsilyloxypropyl)-14beta-androsta-1,4-dien-3-one (54)

2.48 g of the silyldienol ether prepared under a) is suspended as crude product in 30 ml of absolute acetonitrile and mixed with 1 g of palladium(II) acetate. After stirring for 1 more hour at room temperature, the reaction mixture is suctioned off over Celite and the filtrate is concentrated by evaporation in a vacuum. 2.31 g of the above dienone 54 is obtained as crude product.

c 2.31 g of the dienone produced under b) is dissolved in 30 ml of absolute methanol and mixed with 2.3 g of anhydrous potassium carbonate. The mixture is stirred for 1 more hour at room temperature under protective gas, then poured onto saturated sodium chloride solution and extracted several times with methylene chloride. The combined organic phases are washed with saturated sodium chloride solution, dried on sodium sulfate and concentrated by evaporation in a vacuum.

Chromatography of the residue on silica gel with a mixture of ethyl acetate/hexane results in 510 mg of title compound 55.

$^1$H-NMR(CDCl$_3$+Py x d$_5$) δ: 0.57(3H,s,18-H); 2.92(6H,s,NMe); 3.70 (2H,m,CH.O-H); 6.14(1H,s,4-H); 6.15(1H,d,J=10Hz,2-H); 7.00 (1H,d,J=10Hz,1-H); 6.4–7.3(3H,3m,protons on the aromatic substance)

EXAMPLE 12

11beta,19-(4-Dimethylamino-o-phenylene)-17alpha-hydroxy-17-(1-propinyl)-14beta-androsta-4,6-dien-3-one (59)

a)

11beta,19-(4-Dimethylamino-o-phenylene)-14beta-androst-4-en-3,17-dione (56)

4.1 g of above enone 56 is obtained from 6.0 g of compound 47 described under example 9b) in 300 ml of acetone and 15 ml of 4N hydrochloric acid according to the general instructions 1 after 5 hours of stirring at room temperature.

b)

11beta,19-(4-Dimethylamino-o-phenylene)-3-ethoxy-14beta-androsta-3,5-dien-17-one (57)

4.1 g of the product obtained under a) is taken in a mixture of 100 ml of absolute methylene chloride, 9 ml of ethanol and 10 ml of orthoformic acid triethyl ester and mixed with 1.9 g of p-toluenesulfonic acid (monohydrate) at 0° C. Then it is stirred for 3 more hours at ice-bath temperature, then mixed with an excess of sodium bicarbonate solution and the aqueous phase is extracted with methylene chloride. After washing (sodium chloride solution) and drying (sodium sulfate) of the organic phases, it is concentrated by evaporation in a vacuum. Crystallization from ethanol (about 10 ml) yields 1.7 g of the above compound.

c)

11beta,19-(4-Dimethylamino-o-phenylene)-3-ethoxy-17-(prop-1-inyl)-14beta-androsta-3,5-dien-17alpha-ol (58)

150 ml of absolute tetrahydrofuran is saturated at 0° C. with propine. Then 1.6 of M n-butyllithium solution (hexane) (28.8 ml) is slowly instilled in this solution. It is stirred for 30 more minutes and a solution of 1.7 g of the product prepared under b) in 29 ml of absolute tetrahydrofuran is instilled in the reaction mixture. After stirring for 30 more minutes, it is poured onto water, extracted with ethyl acetate and the combined organic phases are washed with sodium chloride solution. After drying (sodium sulfate), concentration by evaporation in a vacuum and chromatography on aluminum oxide (neutral, step III), 0.99 g of the above compound is obtained.

d 0.99 g of the product obtained according to c) is taken in 100 ml of methylene chloride at −50° C. and mixed with 0.34 ml of triethylamine and then with 409 mg of N-bromosuccinimide. It is stirred for 30 more minutes at −40° C., then poured onto sodium sulfate solution and extracted several times with methylene chloride. After drying on sodium sulfate, concentration by evaporation in a vacuum and chromatography on silica gel, 240 mg of slightly impure 11beta,19-(4-dimethylamino-o-phenylene)-17alpha-hydroxy-17-(1-propinyl)-6beta-bromo-14beta-androst-4-en-3-one is isolated. After dissolving of the product in 3 ml of absolute dimethylformamide, 91 mg of lithium bromide and 57 mg of lithium carbonate are added under argon and stirred for 1 hour at 100° C. After cooling of the reaction mixture to room temperature, it is poured onto water, neutralized with 4N hydrochloric acid, cooled to 0° C., stirred for one more hour at this temperature and the precipitated steroid is suctioned off. Chromatography on silica gel with hexane/ethyl acetate yields 170 mg of title compound 59.

$^1$H-NMR(CDCl$_3$+Py x d$_5$) δ: 0.55(3H,s,18-H), 1.90(3H,s,Me);2.90(6H,s,NMe$_2$); 5.75(1H,s,4-H);6.15-6.25(2H,m,6-H,7-H); 6.4-7.3(3H,3m,protons on the aromatic substance)

EXAMPLE 13

11beta,19-(4-Dimethylamino-o-phenylene)-17alpha-hydroxy-17alpha-methyl-17-(1-propinyl)-14beta-androst-4-en-3-one (60)

A Grignard solution is prepared in the usual way from 90 mg of magnesium chips and 0.23 ml of methyl iodide in 4 ml of absolute ether. After addition of 19 mg of copper(I) chloride at 0° C. it is stirred for 30 more minutes and then a solution of 150 mg of product 59 prepared under example 12d) in 2 ml of absolute tetrahydrofuran is instilled. It is stirred for 2 hours at 0° C., poured onto saturated ammonium chloride solution, extracted with ethyl acetate, washed with dilute ammonia solution and then with saturated sodium chloride solution, dried and concentrated by evaporation in a vacuum. After chromatography of the crude product on silica gel, 36 mg of above title compound 60 is isolated.

$^1$H-NMR(CDCl$_3$+Py x d$_5$) δ:0.56(3H,s,18-H); 0.90(3H,d,J=7Hz, 7alpha-Me); 1.90 (3H,s,Me); 2.92 (6H,s,NMe$_2$); 5.82 (1H,s,4-H); 6.4-7.3(3H,3m,protons on the aromatic substance)

EXAMPLE 14

17alpha-Hydroxy-17-(3-hydroxyprop-(Z)-1-enyl)-11beta-[4-(3-pyridyl)-phenyl]-14beta-estra-4,9-dien-3-one (69) (Table 2)

a)

3,3(2,2-Dimethyltrimethylenedioxy)-11beta-[4-(3-pyridyl)phenyl]-9-estrene-5alpha,17beta-diol (61)

10.6 g of above compound 61 is obtained, as described under example 2a), from 3.57 g of magnesium chips in 150 ml of absolute tetrahydrofuran, 3.2 g of 1-bromo-4-(3-pyridyl)-benzene [preparation following example 14] in 100 ml of absolute tetrahydrofuran, 380 mg of copper(I) chloride and 10.0 g of 5alpha,10alpha-epoxy-3,3(2,2-dimethyltrimethylenedioxy)-9(11)-estren-17-ol in 80 ml of absolute tetrahydrofuran.

b)

3,3(2,2-Dimethyltrimethylenedioxy)-5alpha-hydroxy-11beta-[4-(3-pyridyl)-phenyl]-9-estren-17-one (62)

6.82 g of above compound 62 is obtained, as described under example 2b), from 10.6 g of compound 61 prepared under a) in 180 ml of toluene, 5.26 g of aluminum isopropylate and 36.6 ml of cyclohexanone.

c)

3,3(2,2-Dimethyltrimethylenedioxy)-5alpha-hydroxy-11beta-[4-(3-pyridyl)-phenyl]-9,15-estradien-17-one (64)

7.5 g of 3,3(2,2-dimethyltrimethylenedioxy)-11beta-[4-(3-pyridyl-phenyl]-17-trimethylsilyloxy-9,16-estradien-5alpha-ol (63) is obtained, as described under example 2c), raw from 6.82 g of compound 62 prepared under b), 38 mmol lithium diisopropylamide and 9.06 ml chlorotrimethylsilane. Analogous reaction with 3.9 g of palladium(II) acetate yields, after working up, 5.60 g of above compound 64.

d)

3,3(2,2-Dimethyltrimethylenedioxy)-5alpha-hydroxy-11beta-[4-(3-pyridyl)-phenyl]-14beta-estra-9,15-dien-17-one (65)

3.2 g of above compound 65 is obtained, as described under example 2d), is obtained from 5.60 g of compound 64 prepared under c), 600 ml of ethyl acetate, 40 ml of triethylamine and 250 g of silica gel, after chromatography on 550 g of silica gel.

e)

3,3(2,2-Dimethyltrimethylenedioxy)-5alpha-hydroxy-11beta-[4-(3-pyridyl)-phenyl]-14beta-estr-9en-17-one (66)

A solution of 3.39 g of compound 65, produced under d), in 155 ml of ethanol is hydrogenated with 0.68 g of palladium/calcium carbonate (5% Pd). Filtration on Celite and removal of the solvent in a vacuum yields, after chromatography with hexane/ethyl acetate on aluminum oxide, 2.62 g of above compound 66.

f)

3,3(2,2-Dimethyltrimethylenedioxy)-17-[3-tetrahydropyran-2-yloxy)-1-propinyl]-11beta-[4-(3-pyridyl)-phenyl]-14beta-estr-9-en-5alpha,17alpha-diol (67)

2.3 g of above compound 67 is obtained, after column chromatography, as described under example 9c), from 6.95 g of 3-(tetrahydropyran-2-yloxy)-1-propine in 245 ml of absolute tetrahydrofuran, 31 ml of a 1.6M solution of n-butyllithium (hexane) and 2.62 g of compound 66, produced under e), in 53 ml of tetrahydrofuran.

g)

3,3(2,2-Dimethyltrimethylenedioxy)-17-[3-(tetrahydropyran-2-yloxy)-prop-(Z)-1-enyl]-11beta-[4-(3-pyridyl)-phenyl]-14beta-estr-9-ene-5alpha,17alpha-diol (68)

900 mg of compound 67 produced under f) is dissolved in 10 ml of ethanol and mixed with 0.9 ml of pyridine and 90 mg of palladium/barium sulfate (10% Pd). Then it is hydrogenated with hydrogen at normal pressure. After absorption of an equivalent of hydrogen, the catalyst is separated by filtration over Celite, the filtrate is concentrated by evaporation and the residue is chromatographed on aluminum oxide with a mixture of ethyl acetate/hexane. 700 mg of above compound 68 is isolated.

h

Title compound 69 is obtained according to general instructions 2 (Table 2).

Preparation of the Aryl Bromide 4-(3-pyridyl)-phenol 26.8 g of 4-bromophenol was taken under protective gas in 1000 ml of dioxane, mixed with 90 g 3-tributylstannylpyridine [preparation according to litt.: Org. Magn. Resonance, 7 (1975), 610] and 11.1 g of bis-(triphenylphosphine)-palladium(II) chloride and refluxed for 15 hours. After concentration by evaporation in a vacuum and purification on silica gel, 15.92 g of the above compound is isolated.

4-(3-Pyridyl)-1-trifluoromethylsulfonyloxy)-benzene 15.92 g of the above compound and 55.0 g of 4-dimethylaminopyridine are taken under argon at −78° C. in 900 ml of methylene chloride and mixed with 19.8 ml of trifluoromethanesulfonic acid anhydride, dissolved in 300 ml of absolute methylene chloride, by instillation. After 30 minutes, the reaction mixture is poured onto saturated sodium bicarbonate solution. After another 30 minutes, it is extracted with methylene chloride, the organic phases are washed with sodium chloride solution, dried on sodium sulfate and concentrated by evaporation in a vacuum. After chromatography on silica gel, 26.0 g of the above compound is isolated.

4-(3-Pyridyl)-1-tri-n-butylstannyl-benzene 21.4 g of the above compound is obtained, as described under example 5a), after column chromatographic purification on aluminum oxide, from 26.0 g of the above compound in 1300 ml of dioxane, 127.8 ml of hexabutylditin, 10.72 g of lithium chloride and 3.84 g of tetrakis-(triphenylphosphine)- palladium.

1-Bromo-4-(3-pyridyl)-benzene 21.4 g of the above compound in 220 ml of carbon tetrachloride is mixed, by instillation, with 2.44 ml of bromine with vigorous stirring at −40° C. under argon. It is allowed to come to room temperature, washed with sodium chloride solution, dried on sodium sulfate and concentrated by evaporation in a vacuum. After chromatography on aluminum oxide, 10.2 g of the above compound is isolated.

EXAMPLE 15

11beta-[4-(3-Pyridyl)-phenyl]-17alpha-hydroxy-17-(3-hydroxypropyl)-14beta-estra-4,9-dien-3-one (71) (Table 2)

a)

3,3(2,2-Dimethyltrimethylenedioxy)-17-[3-(tetrahydropyran-2-yloxy)-propyl]-11beta-[4-(3-pyridyl)-phenyl]-14beta-estr-9-ene-5alpha,17alpha-diol (70)

632 mg of above compound 70 is obtained, after pressure hydrogenation (60 bars, room temperature) and the usual working up, from 1.4 g of compound 67 prepared under example 14f) in 57 ml of ethanol and 140 mg of palladium/carbon (10% Pd).

b

Title compound 71 is obtained according to general instructions 2 (Table 2).

EXAMPLE 16

11beta-(4-(3-Pyridyl)-phenyl)-14beta-estra-4,9-dien-(17alpha,1′-spiro-17,2′)-tetrahydrofuran-3-one (72)

135 mg of title compound 72 is obtained, as described under example 10), from 175 mg of compound 71 prepared under example 15) in 10 ml of methylene chloride, 0.5 ml of triethylamine and 206 mg of p-toluenesulfonic acid chloride.

$[\alpha]_D^{22} = 201.0°$ (CHCl$_3$; c=0.505)

TABLE 1

| Example | Batch x[g] | y[ml] | z[ml] | Reaction Parameters t[°C.] | a[min] | Yield b[g] | $[\alpha]_D^{20}$(CHCL$_3$) |
|---|---|---|---|---|---|---|---|
| 5 | 0.48 Steroid 5d (31) | 30 | 1.2 | 50 | 30 | 0.26 Steroid Bsp. 5 (32) | 125.4(c = 1.87) |
| 6 | 0.55 Steroid 6b (33) | 30 | 1.4 | 45 | 60 | 0.26 Steroid Bsp. 6 (34) | 106.0(c = 0.52) |
| 7 | 0.76 Steroid 7b (35) | 40 | 1.9 | 50 | 120 | 0.34 Steroid Bsp. 7 (36) | 157.4(c = 0.51) |
| 8 | 0.72 Steroid 8b (37) | 40 | 1.9 | 50 | 30 | 0.33 Steroid Bsp. 8 (38) | 161.5(c = 0.52) |
| 9 | 0.98 Steroid 9F (50) | 50 | 2.5 | 25 | 240 | 0.67 Steroid Bsp. 9 (51) | 134.5(c = 0.52) |

TABLE 2

| Example | Batch c[g] | y[ml] | Reaction Parameters t[°C.] | z[min] | Yield a[g] | $[\alpha]_D^{22}$(CHCl$_3$) |
|---|---|---|---|---|---|---|
| 14 | 0.70 Steroid 14h (68) | 9 | 50 | 60 | 0.33 Steroid Bsp. 14 (69) | 253.5(c = 0.52) |
| 15 | 0.63 Steroid 15b (70) | 8 | 50 | 60 | 0.35 Steroid Bsp. 15 (71) | 222.6(c = 0.2) |

Bsp. = example

We claim:
1. An 11β-phenyl-14β-H-steroid of formula I

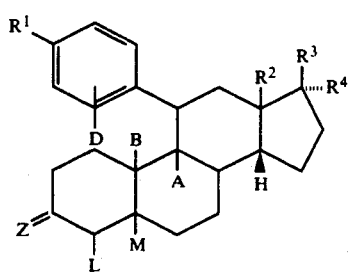

(I)

wherein
Z is O or a hydroxyimino group N∼OH;
L and M either
  together are an additional bond, or
  L is H and M is α-OH; and
either
  A and B together are an additional bond and D is H, and
R$^1$ is
  a) a heteroaryl radical of formula Ia

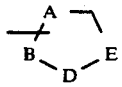

(Ia)

wherein
A is N, O or S, and
B—D—E is C—C—C, N—C—C or C—N—C; or
b) a heteroaryl radical of formula Ib

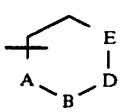

(Ib)

wherein

A is N, and

B—D—E is C—C—C, N—C—C, C—N—C or C—C—N; or c) is cycloalkyl, cycloalkenyl or aryl radical Ic; or A is H and B and D together are a methylene group bridging the C-10 atom of the steroid skeleton and the ortho-carbon atom of the 11β-phenyl ring, and Z is as defined above or is H,H, and $R^1$ is as defined above in a), b) or c) or is d) a $C_{1-10}$-straight-chain, -branched, -saturated or -unsaturated hydrocarbon radical Id, or e)

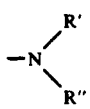

wherein

R' and R" are H or $C_{1-4}$-alkyl, or

R' and R" together with the N atom are a 5- or 6-membered heterocyclic ring, optionally containing an additional heteroatom O, N or S in the ring, or a corresponding tertiary N oxide or acid addition salt thereof; or f) OR''', wherein R''' is H or $C_{1-8}$-alkyl; or g) $SR^{IV}$, wherein $R^{IV}$ is R'''; or h) a $C_{1-10}$-straight-chain, -branched, -saturated or -unsaturated hydrocarbon radical substituted by one or more oxo, hydroxyimino, $C_{1-10}$-alkanoyloxy or $OR^V$ groups, wherein $R^V$ is H or $C_{1-8}$-alkyl;

wherein any heteroaryl radical of formula Ia is optionally substituted by one or more halogen radicals and/or one or more $C_{1-2}$-alkyl radicals, and any cycloalkyl, cycloalkenyl or aryl radical Ic is optionally substituted by one or more halogen, optionally protected hydroxy, alkoxy, optionally in the form of the sulfoxide or sulfone and/or of the N oxide, oxidized alkylthio and/or dialkylamino radicals;

$R^2$ is a methyl or ethyl radical;

$R^3$ and $R^4$ are each, respectively

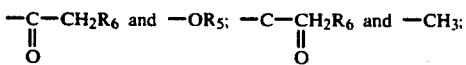

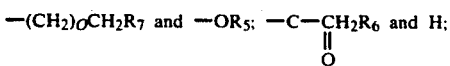

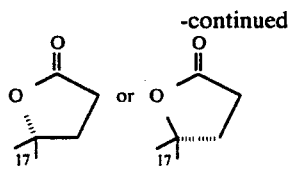

wherein $R_5$ is H or a $C_{1-4}$-alkanoyl group,

Y is H, a Cl, I or Br atom, an alkyl, hydroxyalkyl, alkoxyalkyl or alkanoyloxyalkyl group having 1-4 C atoms in the alkyl or alkanoyl radical;

$R_6$ is H, OH, or a $C_{1-4}$-alkyl, —O-alkyl, or —O-alkanoyl group;

O is 0, 1, 2 or 3;

$R_7$ is a hydroxy or cyanide radical, or a $C_{1-4}$-O-alkyl or —O-alkanoyl group;

k is 0, 1 or 2;

Q is O or H,H.

2. A 13-alkylgonane of claim 1, wherein the heteroaryl radical of formula Ia is a 3-thienyl, 3-furyl or 3-pyrrolyl radical.

3. A 13-alkylgonane of claim 1, wherein the heteroaryl radical of formula Ib is a 3- or 4-pyridyl, 5-pyrimidine, 4-pyridazine or pyrazine radical.

4. A 13-alkylgonane of claim 1, wherein the cycloaryl, cycloalkenyl or aryl radical Ic is a cyclohexyl, cyclohexenyl or phenyl radical.

5. A 13-alkylgonane of claim 1, wherein the alkenyl radical Id contains up to three double bonds.

6. A 13-alkylgonane of claim 1, wherein the heteroaryl radical of formula Ia is substituted by a Cl or Br atom.

7. A 13-alkylgonane of claim 1, wherein the heteroaryl radical of formula Ia is substituted by a $C_{1-3}$-alkyl radical.

8. A 13-alkylgonane of claim 1, wherein the cycloalkyl, cycloalkenyl or aryl radical Ic is substituted by one or two Cl and/or Br atoms.

9. A 13-alkylgonane of claim 1, wherein the cycloalkyl, cycloalkenyl or aryl radical Ic is substituted by one or two optionally protected hydroxy and/or $C_{1-8}$-alkoxy radicals.

10. A pharmaceutical preparation comprising an effective amount of a 13-alkylgonane of claim 1 and a pharmaceutically acceptable excipient.

11. A method of treating hormone-dependent tumors, comprising administering an effective amount of a compound of claim 1.

12. A method of claim 11, wherein the hormone-dependent tumor contains progesterone receptors.

13. A method of inducing abortion, comprising administering an effective amount of a compound of claim 1.

14. A method of post-coital fertility control, comprising administering an effective amount of a compound of claim 1.

15. A method of inducing menstruation, comprising administering an effective amount of a compound of claim 1.

16. A method of inducing labor, comprising administering an effective amount of a compound of claim 1.

* * * * *